United States Patent
Horn et al.

(10) Patent No.: US 9,670,524 B2
(45) Date of Patent: *Jun. 6, 2017

(54) TEST ELEMENTS FOR DETERMINING AN ANALYTE CONCENTRATION THAT INCLUDE CORRECTION INFORMATION FOR AT LEAST ONE INTERFERING VARIABLE

(71) Applicant: Roche Diabetes Care Inc., Indianapolis, IN (US)

(72) Inventors: Carina Horn, Biblis (DE); Volker Unkrig, Ladenburg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,483

(22) Filed: Dec. 7, 2015

(65) Prior Publication Data

US 2016/0083777 A1 Mar. 24, 2016

Related U.S. Application Data

(60) Division of application No. 14/310,438, filed on Jun. 20, 2014, now Pat. No. 9,255,286, which is a continuation of application No. PCT/EP2012/076361, filed on Dec. 20, 2012.

(30) Foreign Application Priority Data

Dec. 22, 2011 (EP) .................................... 11195083

(51) Int. Cl.
| | |
|---|---|
| C12Q 1/54 | (2006.01) |
| A61B 5/145 | (2006.01) |
| G01N 33/52 | (2006.01) |
| A61B 5/1486 | (2006.01) |
| G01N 21/84 | (2006.01) |
| G01N 21/78 | (2006.01) |
| G01N 35/00 | (2006.01) |
| G01N 21/77 | (2006.01) |

(52) U.S. Cl.
CPC .............. *C12Q 1/54* (2013.01); *A61B 5/1486* (2013.01); *A61B 5/14532* (2013.01); *A61B 5/14535* (2013.01); *A61B 5/14546* (2013.01); *G01N 21/78* (2013.01); *G01N 21/8483* (2013.01); *G01N 33/525* (2013.01); *A61B 2562/0295* (2013.01); *G01N 2021/7786* (2013.01); *G01N 2035/00108* (2013.01)

(58) Field of Classification Search
None
See application file for complete search history.

(56) References Cited

U.S. PATENT DOCUMENTS

| | | | |
|---|---|---|---|
| 4,250,257 A | 2/1981 | Lee et al. | |
| 5,843,691 A | 12/1998 | Douglas et al. | |
| 6,036,919 A | 3/2000 | Thym et al. | |
| 6,194,221 B1 * | 2/2001 | Rehg | G01N 33/54386 |
| | | | 422/423 |
| 7,548,773 B2 | 6/2009 | Noble | |
| 8,574,514 B2 | 11/2013 | Petrich et al. | |
| 9,255,286 B2 * | 2/2016 | Horn | G01N 21/78 |
| 2010/0292932 A1 | 11/2010 | Won | |

FOREIGN PATENT DOCUMENTS

| | | |
|---|---|---|
| EP | 0821234 B1 | 10/2002 |
| EP | 1281352 A1 | 2/2003 |
| WO | WO2005112742 A3 | 3/2006 |
| WO | 2010052306 A1 | 5/2010 |
| WO | 2010052307 A3 | 7/2010 |

* cited by examiner

*Primary Examiner* — Ralph Gitomer

(57) ABSTRACT

Test elements are disclosed for detecting at least one analyte concentration in a sample. The test elements are used for detecting one or more analytes such as metabolites in body fluids, especially glucose. The test elements correct for an interfering variable such as temperature and or hematocrit in a test element system via a correction factor based upon diffusion of at least one diffusable label.

16 Claims, 13 Drawing Sheets

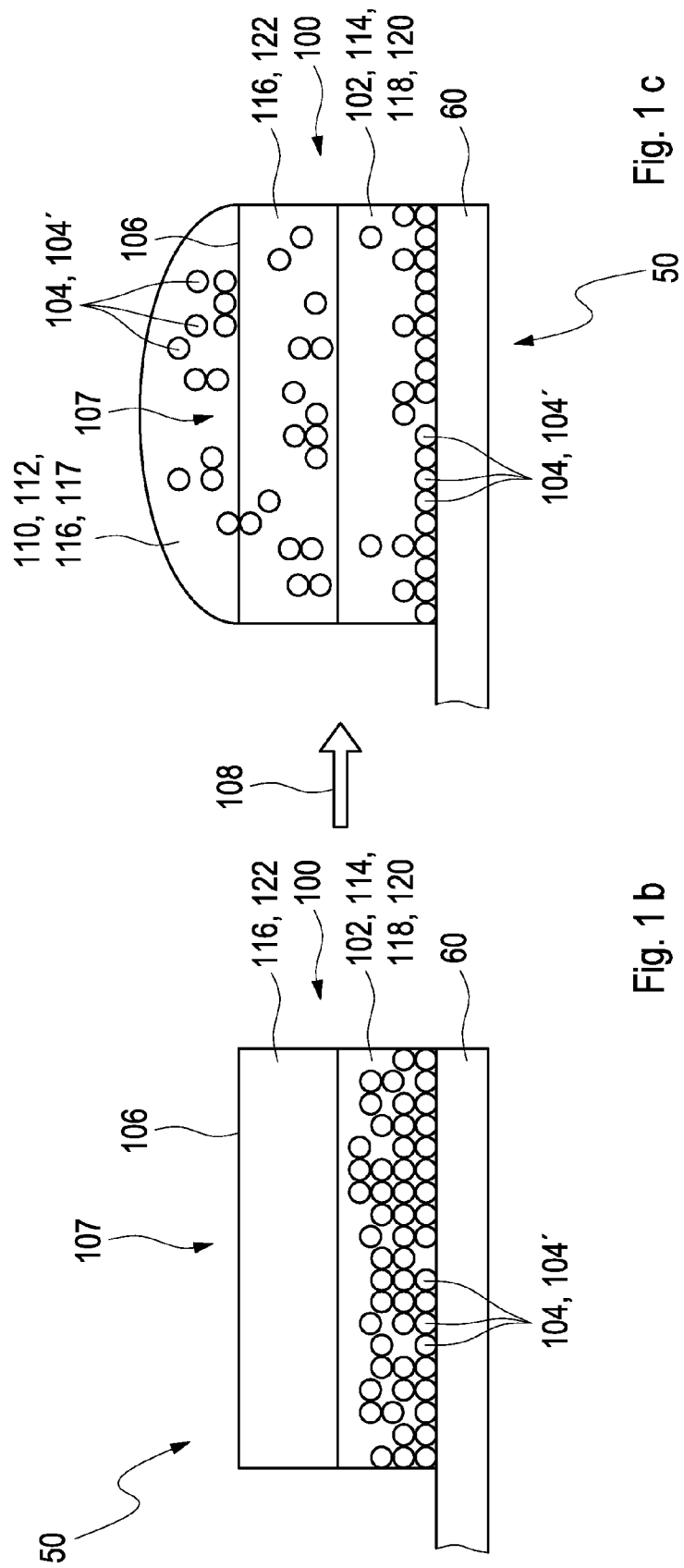

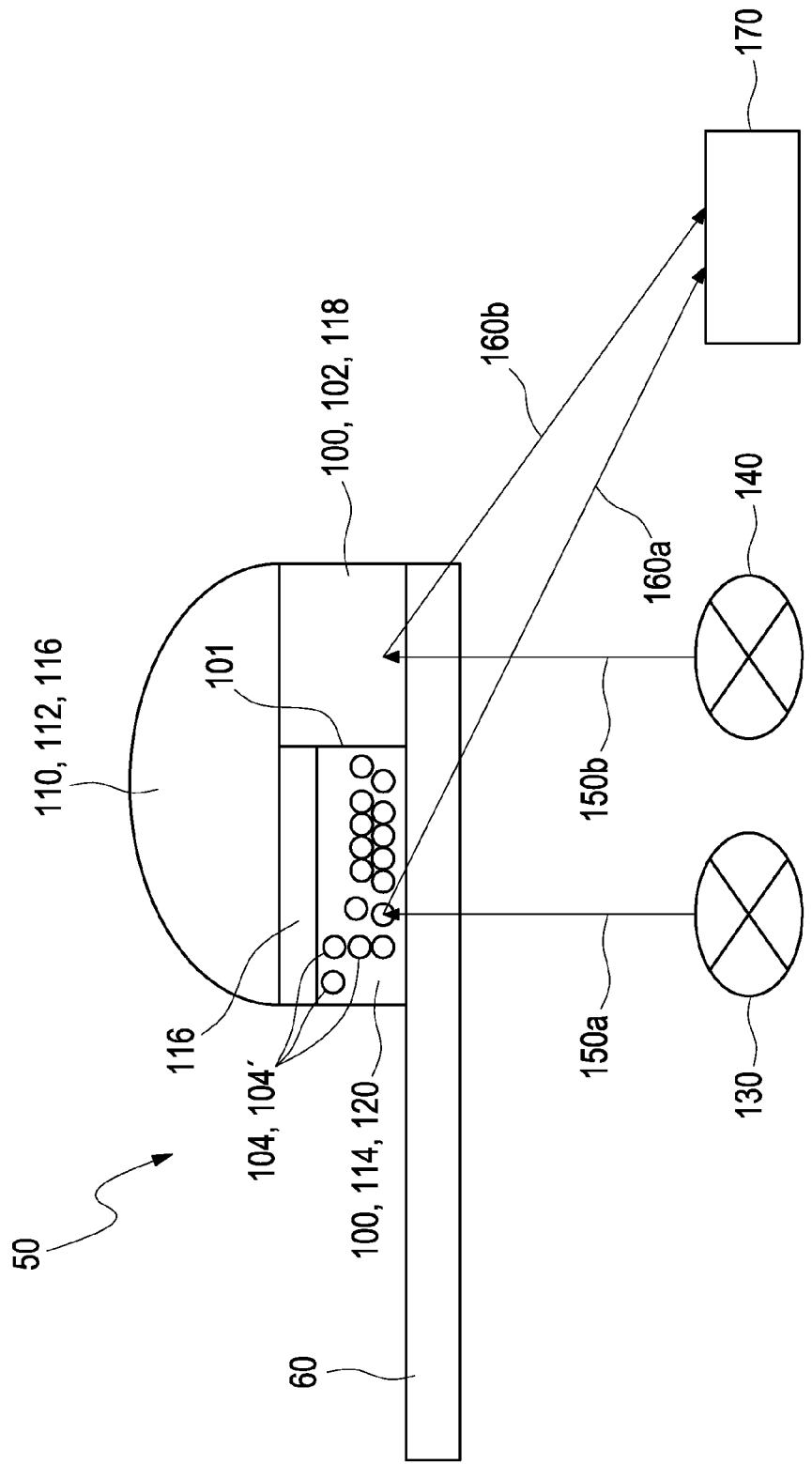

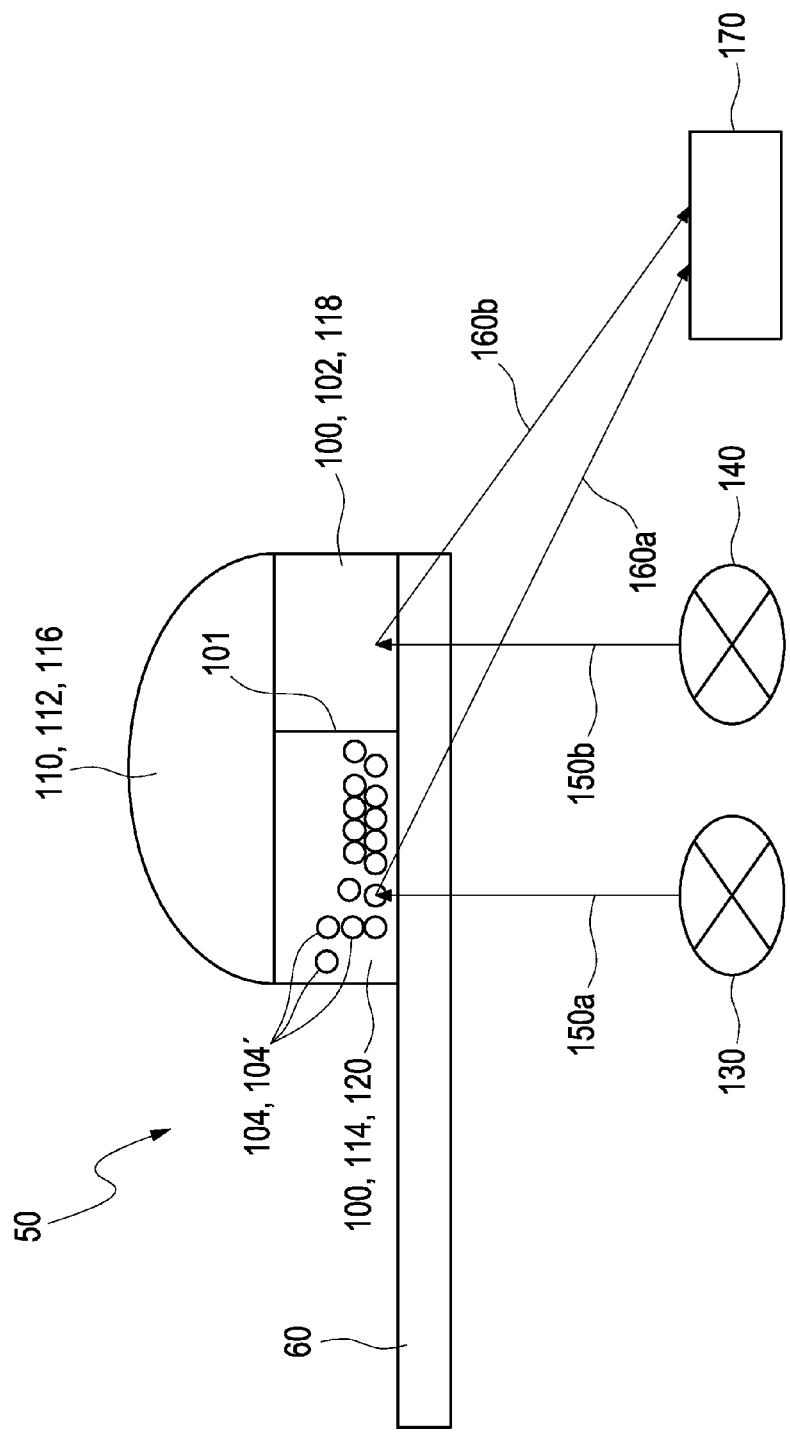

TEST ELEMENTS FOR DETERMINING AN ANALYTE CONCENTRATION THAT INCLUDE CORRECTION INFORMATION FOR AT LEAST ONE INTERFERING VARIABLE

CROSS-REFERENCE TO RELATED APPLICATIONS

This patent application is a divisional of U.S. patent application Ser. No. 14/310,438 (filed 20 Jun. 2014), now U.S. Pat. No. 9,255,286 (issued 9 Feb. 2016), which is continuation of Int'l Patent Application No. PCT/EP2012/076361 (filed 20 Dec. 2012), and which claims priority to and the benefit of EP Patent Application No. 11195083.8 (filed 22 Dec. 2011). Each patent application is incorporated herein by reference as if set forth in its entirety.

TECHNICAL FIELD

This disclosure relates generally to chemistry and medical diagnostics, and more particularly, it relates to methods of correcting temperature-dependence and/or hematocrit-dependence of a test element system when determining an analyte concentration via a correction factor based upon diffusion of a diffusable label.

BACKGROUND

In many areas of the natural sciences and technology, it is necessary to reliably and rapidly detect in a liquid and/or gaseous sample one or more analytes in a qualitative and/or quantitative manner. For example, as part of preventive diabetes care and/or diabetes treatment, it is generally necessary to determine blood sugar level at least once a day, generally multiple times, to guide individuals having diabetes to take appropriate countermeasures if deviations from a normal value or range occur.

So that the daily routine of such individuals is not compromised any more than is necessary, devices and methods have been developed that allow blood sugar measurements not only in a clinical environment but also in the workplace or home, as well as during leisure activities. Such devices and methods generally are based on using one or more disposable test elements, which are known and available in different forms. For example, test elements can be in the form of test strips, test tapes, test disks, test needles or in other forms.

Test elements often include one or more test fields having at least one analyte-specific detection reagent as part of the test chemistry. The detection reagent is selected and designed for carrying out a detectable reaction in the presence of the analyte of interest. Examples of commercially available test elements include, but are not limited to, Accu-Chek® Aviva, Accu-Chek® Performa, Accu-Chek® Active, Accu-Chek® Go or Accu-Chek® Mobile test cassette with appropriate test instruments such as Accu-Chek® Aviva, Active, Go and Mobile from Roche Diagnostics Operations, Inc. (Indianapolis, Ind.)

Intl Patent Application Publication No. WO 2010/052306 describes a diagnostic test element for detecting an analyte of interest in a body fluid sample. The test element includes a test field having a detection reagent configured to undergo a detectable optical change in the presence of the analyte. The test field has at least one detection layer that includes the detection reagent and that has particles with at least 90% of all the particles of the detection layer having an actual particle size of less than 10 μm.

Likewise, Int'l Patent Application Publication No. WO 2010/052307 describes a test element for detecting an analyte of interest in a sample. The test element includes at least one test field having a test field surface and having a detection reagent configured to carry out a detectable reaction in the presence of the analyte. In addition, the test element has at least one distribution element having at least one distribution surface facing the test field surface with at least one capillary gap being formed between the distribution surface and the test field surface. In test elements, it is possible to use one or more different test chemistries, such as an enzyme system, to convert and detect the analyte.

To provide a user with a manageable form of the enzyme system, the enzyme system can be introduced or immobilized on the test element in a dry and solid layer(s) as at least part of the test chemistry together with further reactive substances such as a mediator. The user only has to apply the sample to the layer to obtain a measurement result shortly thereafter. As such, after the sample is applied to the layer of the test element, the analyte-specific detection reaction proceeds both in the layer and completely or partly in the sample. For example, one or more reactive substances in the form of the detection reagent or constituents thereof can dissolve in the sample and can be observed up to an end point of the reaction.

These methods also can involve diffusion processes, in which the sample transports the analyte to the reactive substances and/or the detection substance formed diffuses into or out of a detection layer. For example, the end point of the reaction can be determined in electrochemical or optical systems. In this manner, the rate of formation of a detection substance can be equal to the rate of diffusion of the detection substance formed. Alternatively, a measurement signal, from which the analyte concentration can be derived, is determined at a particular time after applying the sample to the test field.

Such diffusion processes, as well as enzyme-catalyzed reactions, may be temperature-dependent. In addition, further constituents of the sample, such as cellular and/or particulate constituents (e.g., red blood cells) may have an influence on the diffusion and dissolution processes in the test element. The result can be a heavy dependence of the measured analyte concentration on the ambient temperature at which the measurement is carried out, as well as on the hematocrit (Hct) of the sample applied to the test element. Thus, in principle, there might be the risk of analyte concentration being influenced, and this in turn can lead to a challenge when dosing medicaments such as insulin. Especially in low concentration ranges of analytes, such as blood glucose in the case of a diabetic, an incorrectly high measured blood glucose can lead to too much insulin being administered. Therefore, it is important to correct the temperature-dependence and/or Hct-dependence of the particular test element system.

For example, temperature can be measured by a sensor accommodated in the measurement instrument and used to correct analyte concentration. However, this can in turn lead to faulty corrections, since temperature generally is not measured at the actual position of the chemical reaction of the analyte. Consequently, the temperature used for correction can differ from the temperature of the reaction site of the analyte, and so the correction can in turn lead to errors.

Furthermore, it is difficult to carry out a Hct correction, especially in optical systems since there are generally no purely Hct-dependent measurement values that could be used to correct analyte concentration. With electrochemical systems, however, correcting the measurement signal with regard to Hct is possible but is very laborious owing to a complex pulse sequence method and is additionally superimposed by other interfering signals in the sample.

In this manner, U.S. Pat. No. 4,250,257 describes methods and devices for analyzing whole blood samples. The methods and devices use a gel in which an inert substance is accommodated and diffuses out of the gel into the whole blood sample, whereas plasma of the whole blood sample diffuses into the gel. The diffusion of the inert substance out of the gel is inversely proportional to the Hct of the blood sample. In addition, various possibilities of bringing about a Hct correction are disclosed. In one example, a separate gel can be used to determine Hct, and from this a correction factor subsequently can be used for another blood sample. Alternatively, an analyte detection reaction and a Hct correction can be carried out by means of two different color changes, with a first color change resulting from the analyte detection reaction and with a second color change resulting from diffusion of a dye as inert medium into the sample. Furthermore, a Hct correction using albumin is described with bromocresol green (BCG).

Additionally, U.S. Pat. No. 7,548,773 describes a method of calibrating a measurement system based upon dissolution of an analyte in a reference channel. Owing to the dissolution of a known amount of analyte by sample in the reference channel, it is possible to carry out, in parallel to the actual analyte concentration determination, a differential determination relating to the reference channel to determine the reaction rate of the sample. As a result, corrections can be made on the analyte concentration. However, a disadvantage of this method is the need for dissolving a reference molecule to be determined on a capillary wall. The method also can be influenced by properties of the system that are not associated with the sample. Furthermore, the dissolution and movement of the analyte-identical calibrator is dependent on the analyte concentration. It is not possible to distinguish between influences of analyte concentration and other factors on the movement of the calibrator, and this can in turn lead to falsification of the determined analyte concentration.

For the foregoing reasons, there is a need for additional methods, devices and test elements that correct or compensate for temperature-dependence and/or Hct-dependence of a test element system when determining an analyte concentration.

BRIEF SUMMARY

This disclosure describes devices, test elements and methods of detecting an analyte in a body fluid sample that correct or compensate an analyte concentration for interfering variables that may be present in the body fluid sample, devices and test elements used therein. To address the disadvantages noted above, an inventive concept provided herein is that such interfering variables can be corrected or compensated by detecting diffusion of a diffusable label and incorporating the detected diffusion into correction information that also takes into account an influence of the interfering variable on diffusion of the diffusable label.

It is therefore an object of the present disclosure to provide devices, test elements and methods of detecting at least one analyte in a sample that at least partly avoid the disadvantages of known methods, devices and test elements as discussed above. More particularly, the disclosure provides methods, devices and test elements that at least partly avoid falsification of a measured analyte concentration owing to diffusion effects, even in the case of varying Hct and temperature of the sample or of the test element. A further object is to provide methods, devices and test elements for detecting at least one analyte in a sample that allow analyte-independent detection.

In one aspect, devices are provided that include at least one analyte detector. In addition, the devices include at least one diffusable label detector. In some instances, the devices also include an evaluation unit configured to completely or partly carry out the methods described herein.

In another aspect, test elements are provided that include a test chemistry situated in a detection layer of a test field mounted on a test support of the test element. The test chemistry can be configured for electrochemically or optically detecting the analyte.

In some instances, the test chemistry is a detection reagent that includes at least one enzymatic detection reagent. The detection reagent also can include a mixture of multiple detection reagents or multiple substances that together form the detection reagent that may convert the analyte to a detectable signal. Examples of analyte-specific enzymatic detection reagents include, but are not limited to, oxioreductase enzymes (e.g., GlucDor/PQQ), dehydrogenase enzymes, oxidase enzymes or similar enzymes or combinations thereof. In other instances, the at least one enzymatic detection reagent is glucose oxidase (GOD) or glucose dehydrogenase (e.g., FAD-, NAD+- or PQQ-dependent GDH).

The test chemistry can be in the form of at least one test chemistry layer or at least one detection layer. The at least one test chemistry layer optionally can include substances such as, for example, one or more fillers. In some instances, the filler can be one or more types of particles such as inorganic particles, which are not identical to the detection reagent or at least not completely identical to the detection reagent. The test chemistry layer also can include at least one organic film former.

The test elements also include at least one diffusable label. In some instances, the diffusable label can be a dye and/or can include at least one such dye, the diffusion behavior of which can be ascertained by electrochemical or optical detection methods in the test element, the sample and/or at least part of the sample. In other instances, the diffusable label is a cyanine dye, azo dye, sulfone dye, or a combination of at least two thereof. In still other instances, the diffusable label can be erioglaucine, indigo carmine, hydroxynaphthol blue, 1,1-diethyl-4,4-carbocyanine iodide, amaranth, or a combination of at least two thereof.

The test elements can be designed in a wide variety of configurations. In some instances, the test elements are test strips, test tapes, test needles and/or microsamplers.

In view of the foregoing, methods are provided for determining at least one analyte concentration in a body fluid sample such as blood or interstitial fluid. Alternatively, the method can be used for detecting at least one metabolite in a body fluid sample.

The methods can include a step of performing a calibration measurement to obtain at least one piece of correction information based upon diffusion of a diffusable label, where the at least one piece of correction information accounts for an influence of at least one interfering variable in a body fluid sample and accounts for a general relationship between the at least one interfering variable and diffusion of the diffusable label.

The methods also include a step of detecting diffusion of at least one diffusable label in a body fluid sample or at least part of the body fluid sample having or suspected of having an analyte of interest therein that has been applied to at least one test element as described herein. The at least one piece of correction information is generated from the diffusion of the diffusable label.

The methods also include a step of detecting or measuring an analyte concentration in the body fluid sample with the at least one test element as described herein. Thus, at least one reaction is detected between the test element's test chemistry and the analyte of interest.

The detecting steps can be an electrochemical or optical detectable reaction. However, other types of detection reactions are contemplated.

In some instances, the reaction between the test chemistry and the analyte can be one in which at least one detection substance is formed in the presence of the at least one analyte. In this manner, it is also possible to form and/or use multiple detection substances which can be detected individually, in groups or altogether. Detection substances are in particular substances that are formed owing to the at least one detection reaction and/or that are involved in the at least one detection reaction and which are directly or indirectly detectable. On the basis of the at least one detection substance detected, it is possible, for example, for the at least one analyte to be detected quantitatively and/or qualitatively.

Regardless of whether the detecting step is an electrochemical or optical detectable reaction, at least one signal, which is also referred to as a measurement value, is generated. The at least one signal can be ascertained during and/or after reaction of the test chemistry with the analyte and can be corrected by the at least one piece of correction information. In some instances, the at least one piece of correction information is about the actual temperature and/or the Hct.

The methods also include the step of correcting or compensating the analyte concentration by taking into account the at least one piece of correction information, where the at least one piece of correction information corrects or compensates for at least one interfering variable of the sample. In some instances, the piece of correction information takes into account an influence of at least one of the following interfering variables during the determination of the concentration of the analyte: a temperature of the sample and/or of the test element, a proportion of constituents of at least one substance in the sample such as Hct.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 1b shows a diagram of an exemplary test field containing a diffusable label before wetting of the test field.

FIG. 1c shows a diagram of an exemplary test field containing a diffusable label after wetting of the test field.

FIG. 1e shows a diagram of an exemplary device having an alternative test element.

FIG. 1f shows a modification of the exemplary embodiment according to FIG. 1e.

Figure 1A:
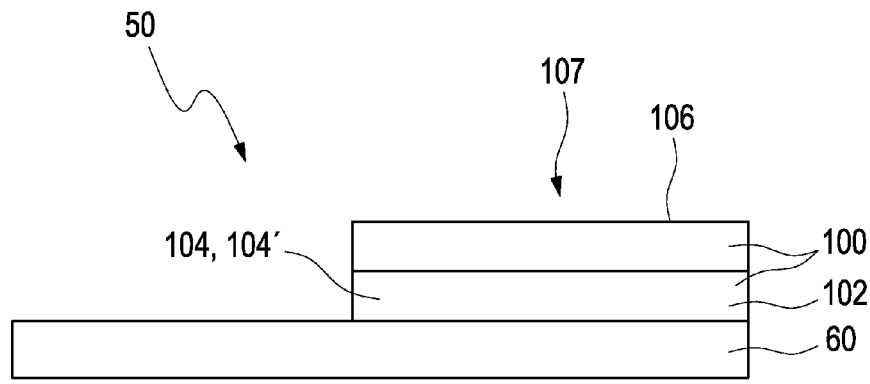
FIG. 1a shows a diagram of an exemplary test element having a test field.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The devices, test elements and methods now will be described more fully hereinafter with reference to the accompanying drawings, in which some, but not all embodiments of the inventive concept are shown. Indeed, the devices, test elements and methods may be embodied in many different forms and should not be construed as limited to the embodiments set forth herein; rather, these embodiments are provided so that this disclosure will satisfy applicable legal requirements.

Likewise, many modifications and other embodiments of the devices, test elements and methods described herein will come to mind to one of skill in the art to which the disclosure pertains having the benefit of the teachings presented in the foregoing descriptions and the associated drawings. Therefore, it is to be understood that the devices, test elements and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the devices, test elements and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Exemplary devices, test elements and methods are provided and are based upon the inventive concept of using a diffusable label to obtain at least one piece of correction information to correct for an interfering variable on an analyte concentration.

As used herein, "piece of correction information" means at least one piece of information about at least one interfering variable, it being possible to derive the piece of information from diffusion of a diffusable label and the interfering variable having, or it being possible for the interfering variable, an influence on determining analyte concentration.

As used herein, "interfering variable" means at least one property or combination of properties of a sample, which property or combination is independent of the actual analyte concentration, and which can influence a detection of a reaction of the test chemistry with the analyte and/or the actual reaction of the test chemistry with the analyte and can influence and/or falsify determining analyte concentration. Likewise, the at least one interfering variable can describe a proportion of at least one interfering component in the sample (i.e., a proportion of at least one substance of the sample), which influences the reaction of the test chemistry with the analyte and/or which influences the detection of the reaction of the test chemistry with the analyte. For example, one interfering variable can be a Hct value of the sample. Alternatively or additionally, the interfering variable can be a temperature of the sample and/or of the environment. Alternatively still, the interfering variable can be Hct and temperature of the sample and/or of the environment. Generally, a reaction of the analyte with the test chemistry is slowed down by lowering the temperature of the sample and/or of the environment. Conversely, the reaction of the analyte is generally increased when Hct in the sample is lowered.

The devices, test elements and methods are useful in a variety of applications. For example, the devices, test elements and methods are useful as diagnostic tools for a variety of analytes. Examples of analytes of interest include, but are not limited to cholesterol, lactate, fructose and glucose. The description below, however, is largely directed toward glucose, as it is generally the most important analyte when monitoring blood of individuals having diabetes. It is to be understood that the inventive concept is transferrable to other analytes of interest.

Devices

Devices of the inventive concept include at least one analyte detector, which can be at least one electrochemical analyte detector and/or at least one optical analyte detector. These types of detectors are known to one of skill in the art.

With respect to electrochemical analyte detectors, they include electrodes that contact the reagent to be analyzed. Electrochemical analyte detectors have at least one, or even two or more, electrodes for electrochemical detection.

With respect to optical analyte detectors, they include at least one photosensitive detector element, such as at least one photodiode formed completely or partly differently from an optional photosensitive detector element of the diffusable label detector as described below. Alternatively or additionally, the photosensitive detector element of the optical analyte detector can be formed completely or partly identically in terms of components to the photosensitive detector element of the diffusable label detector. For example, a common photodiode can be provided that is both a component of the optical analyte detector and a component of the diffusable label detector. If the diffusable label detector and the optical analyte detector share at least one component, it is possible to carry out a temporally separated or staggered detection of the diffusable label and/or of the diffusion of the diffusable label and of the analyte by using a pulsed and/or intermittent measurement scheme in which the diffusion of the label is acquired at particular times by means of the photodiode and the analyte detection is carried out at other times by means of the same photodiode. The optical analyte detector also can include at least one light source such as, for example, at least one light-emitting diode (LED), configured to illuminate at least one test field containing the test chemistry. The at least one light source of the optical analyte detector can be designed completely or partly differently from the at least one light source of the diffusable label detector.

As part of the inventive concept, the devices also include at least one diffusable label detector, which can be at least one electrochemical diffusable label detector and/or at least one optical diffusable label detector. As above, these types of detectors are known to one of skill in the art.

With respect to the electrochemical diffusable label detector, it can include one or more electrochemical detection electrodes.

With respect to the optical diffusable label detector, it can include at least one photosensitive detector element such as at least one photodiode to detect light emitted by a light source. The light source can be at least one LED, it being possible to configure the light source for illuminating at least one test chemistry field containing the diffusable label and/or at least one label field containing the label and/or for illuminating the sample.

In this manner, the light of the light source need not be directed directly onto the detector, but instead can be altered or reflected by various elements, such as, for example, filters, mirrors or the test element.

The light source for the optical detectors can radiate light within any desired wavelength range from about 200 nm and about 1000 nm. In some instances, the light source can radiate light at about 200 nm, about 300 nm, about 400 nm, about 500 nm, about 600 nm, about 700 nm, about 800 nm, about 900 nm or about 1000 nm. Depending on the wavelength range within which the analyte absorbs the light, another wavelength range may be used for detecting the diffusable label. For example, light within a UV light wavelength range from about 200 nm to about 400 nm can be used for exciting the diffusable label when the analyte absorbs light within a wavelength range from about 500 nm to about 1000 nm. Conversely, light within a wavelength rage from about 300 nm to about 400 nm can be used for exciting the analyte when the diffusable label absorbs light within a wavelength range from about 400 nm to about 1000 nm. Other wavelength ranges for the excitation of the analyte or the diffusable label are likewise conceivable.

As used herein, "about" means within a statistically meaningful range of a value or values such as a stated concentration, length, molecular weight, pH, time frame, temperature, volume or wavelength. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The devices also can include at least one evaluation unit in the form of a data processing device. The evaluation unit can be configured to completely or partly carry out the methods as described herein.

Test Elements

Test elements of the inventive concept include a test field having at least one test chemistry. As used herein, "test field" means an element that has a cohesive quantity of test chemistry such as, for example, at least one layer of the test chemistry and also optionally one or more further components.

The at least one test chemistry is configured to carry out at least one detectable reaction with the analyte. As used herein, "test chemistry" means a substance and/or a mixture configured to carry out at least one detectable change of at least one property in the presence of the analyte of interest to be detected. More particularly, the test chemistry can contain at least one reagent that converts the analyte in a detection reaction. Intl Patent Application Publication No. WO 2010/052307 discloses an exemplary test chemistry and detection reagent that may be used in the test elements described herein.

As used herein, "detectable reaction" means a reaction that is detectable by means of at least one physical (i.e., optical) and/or electrochemical detection method. Detectable reactions are known that are based upon detecting the analyte of interest by optical and/or electrochemical means. In this manner, it is possible to use reactions in which at least one detection substance is formed that can be detected optically and/or electrochemically.

One or more detection reagents for detecting the analyte in the sample can be situated in the test chemistry.

The test elements can, in particular, have a form as may be known in the art such as, for example, a test strip, a test tape, a test needle or a microsampler (i.e., an element having at least one needle or lancet and at least one capillary element). However, other forms for the test elements are also possible in principle.

The test elements thus include at least one test field, which can be a two- or three-dimensional region of the test element usable for detecting the analyte. In some instances, the test field is a dry test field. The test field includes the test chemistry having at least one detection reagent configured to carry out a detectable reaction in the presence of the analyte. In addition, the test field can include further substances such as, for example, carriers, auxiliaries, pigments, fillers, buffer substances and the like. In some instances, the detection reagent can include at least one enzymatic detection reagent.

The test elements therefore include at least one test field having at least one test chemistry layer, where the test chemistry layer includes the test chemistry such as at least one enzyme. Examples of enzymes for use in the test fields include, but are not limited to, glucose dehydrogenase and glucose oxidase.

As noted above, the at least one test chemistry can be in the form of a test chemistry layer. The test chemistry layer can, for example, be designed analogously to the first film layer of the test element as described in EP Patent No. 0 821 234.

The test chemistry layer also can include at least one organic film former such as, for example, a polyvinyl proprionate dispersion. Alternatively or additionally, other film formers may be used.

As part of the inventive concept, the test element also includes at least one diffusable label, where the at least one diffusable label is situated in at least one first region of the test element, and where the diffusable label is configured to diffuse at least partly from the first region of the test element into at least one second region As used herein, "diffusable label" means a detectable chemical substance that is at least locally determinable by electrochemical and/or optical detection methods.

The at least one diffusable label is chemically different from the at least one analyte of interest. As used herein, "chemically different" mean that the individual molecule of the label deviates by at least one atom from the analyte of interest. For example, the molecule of the label can have at least one atom more or less than the analyte of interest. Alternatively, "chemically different" means that the number and sequence of atoms in the diffusable label are identical to the sequence of atoms in the analyte of interest, but the spatial arrangement of atoms is not identical at every position, as occurs, for example, in the case of compounds having asymmetric carbon atoms (i.e., two enantiomers of a same molecule). For instance, one possibility would be to use two enantiomers, one of the enantiomers representing the analyte and the other enantiomer representing the diffusable label.

As used herein "diffusable label different from the analyte of interest" means a label that is at least partly non-identical to the analyte of interest. For example, by the label having at least one chemical substance that is not in the analyte of interest that is to be detected.

As used herein, "locally" means a defined area or a defined volume of the test field used for detecting the diffusable label. For example, and with respect to optically detecting the diffusable label, the area or the volume can be defined by the form of the incident light or by the positioning of the detector. With respect to electrochemically detecting the label, it is possible for the area or the volume to be defined by the form and arrangement of the electrode.

As noted above, the at least one diffusable label can be situated in one region of the test field or in a further region of the test element, where the at least one diffusable label is configured to diffuse at least partly from the at least first region of the test element into at least one second region. The second region can be a region within the test field or outside the test field, or within the test element or outside the test element.

One region for this purpose is the supernatant of the sample above the test element. For example, the diffusable label can diffuse from a first region of the test element into a second region that is a supernatant of the sample. The diffusable label can be situated together with the test chemistry in a test chemistry layer and can diffuse into the sample during wetting of the test field of the test element with the sample, into at least one second region that can be either within or outside the test element.

Alternatively or additionally, the diffusable label also can at least be completely or partly arranged outside the test element before contacting of the test element and/or the test chemistry. The label can be designed such that upon contacting the test element with the sample, at least one detectable diffusion of the label occurs in the sample or at least one constituent of the sample. The diffusion can take place in a supernatant of the sample that has not been taken up by the test element and/or the test chemistry such as, for example, a drop-shaped supernatant, and/or in part of the sample that has been taken up by the test element or a part thereof.

As such, the diffusable label can be contained in at least one region of the test elements at least before wetting with sample, where the test chemistry is likewise completely or partly contained in the first region. The region can be referred to as a first region. If the diffusable label is present only in this at least one first region of the test element, the region also can be referred to as a label region. The first region therefore can be designed as a label layer.

In this manner, the test chemistry layer and the diffusable label layer can be identical. Once the sample contacts the diffusable label and the test chemistry, it is possible for both diffusable label and test chemistry in the test element and/or in the sample to diffuse into one or more regions having a lower concentration. Owing to differences in concentration in different regions of the test field, or of the sample, of diffusable label and test chemistry, it is possible for both diffusable label and test chemistry to diffuse into regions of the sample having a lower concentration of these constituents. It is advantageous when diffusion behavior, more particularly diffusion rate, of the diffusable label resembles the diffusion behavior or the diffusion rate of the test chemistry and the analyte. In this manner, it is possible for both the diffusable label and the analyte to be detected in a same region of the test field.

When the diffusable label and the test chemistry are completely or partly situated in a first region of the test element, detecting diffusion of the label can be achieved with the same detector and/or from the same side of the test element. As noted above, this can be carried out both electrochemically and optically. However, it is possible to use at least one distinct detector for both the diffusable label and the test chemistry (i.e., at least one diffusable label detector and at least one analyte detector). For detecting diffusion of the diffusable label, a region of the test element that includes the label before wetting of the test element with sample can be measured, or alternatively, a region of the test element or the sample that does not include any diffusable label before wetting of the label with sample can be measured. In the former, a decrease in label concentration following wetting of the label with sample is consequently measured, whereas in the latter, the increase in concentration of the label in the measured region takes place.

Briefly, the diffusable label can be or can include a substance that is introduced into the test element in addition to the test chemistry. The diffusable label does not react and/or interact with the test chemistry and/or constituents of the test chemistry. This ensures that the diffusion behavior of the diffusable label is substantially independent of the behavior of the test chemistry and/or of the analyte and ensures an independent way of determining properties of the sample to obtain a piece of correction information, thereby increasing accuracy of an analyte concentration determination.

The diffusion behavior of the dye can be ascertained by electrochemical or optical detection methods in the test element, the sample and/or at least part of the sample.

In some instances, the label can include at least one optically detectable substance such as, for example, at least one dye (e.g., at least one inorganic or organic dye). As used herein, "dye" means a substance (i.e., a chemical compound) that can carry out at least one detectable interaction with light in the ultraviolet and/or visible and/or infrared spectral range such as, for example, reflection with change of a wavelength and/or with change of spectral properties of the reflected light, scattering with change of a wavelength and/or with change of spectral properties of the scattered light, fluorescence, phosphorescence or a combination thereof.

As used herein, "optically detectable dye" means a substance having electrons that interact with electromagnetic waves such as a wavelength range from about 100 nm to about 1500 nm (referred to hereinafter as light), from about 100 nm to about 400 nm (also referred to as ultraviolet light), from about 300 nm to about 800 nm (referred to hereinafter as visible light), and/or from about 800 nm to about 1500 nm (also referred to as infrared light). In other instances, the dye interacts with wavelengths of about 100 nm, about 200 nm, about 300 nm, about 400 nm, about 500 nm, about 600 nm, about 700 nm, about 800 nm, about 900 nm, about 1000 nm, about 1100 nm, about 1200 nm, about 1300 nm, about 1400 nm or about 1500 nm. Interactions can be an absorption, fluorescence or phosphorescence. For example, the dye can be selected so that it spectrally influences the electromagnetic waves in at least one wavelength range or at at least one wavelength by the dye selectively absorbing light at one or more wavelengths and/or in at least one wavelength range. This spectral influence ought to be detectable. Alternatively or additionally, the wavelength of the light can be altered so that there is a shift in wavelength from incident light to emitted and optionally detected light. As such, the dye can include an absorption dye and/or a fluorescence dye and/or a phosphorescence dye.

Moreover, the dye can be an organic dye and/or an inorganic dye. Depending on the intended use, it may be advantageous for the dye to have hydrophilic or hydrophobic properties. When using aqueous samples such as body fluids (e.g., blood, plasma, serum, urine or sputum), the dye should be at least to some extent water-soluble. Additionally, the diffusable label has good chemical stability and good light stability and availability.

Examples of dyes that can be used include, but are not limited to, cyanine dyes, azo dyes, sulfone dyes, or combinations of at least two thereof. Owing to their charge distribution within the dye molecule, the dyes are suitable for absorbing light within a particular wavelength range. As a result of the absorption of the light, their position can be made determinable. To this end, light of a particular wavelength can be directed into the region to be detected and, as a result of an increase or decrease in intensity of the reflected light in the region in relation to a preceding time, the presence of the diffusable label and the label diffusing away is made detectable.

Possible cyanine dyes are all cyanine dyes known to one of skill in the art for detection purposes. Specific examples of cyanine dyes include, but are not limited to, streptocyanine or open-chain cyanine, hemicyanine and closed-chain cyanine such as phthalocyanine, formazan, porphyrins and 1,1-diethyl-4,4-carbocyanine iodide, or combinations of at least two thereof.

Possible azo dyes are all azo dyes known to one of skill in the art for detection purposes. Specific examples of azo dyes include, but are not limited to, aliphatic and aromatic azo compounds such as aniline yellow, methyl orange, azobenzene, hydroxynaphthol blue, 4-(dimethylaniline) azobenzene, amaranth, allura red, azorubine, anthocyanins, para red, or combinations of at least two thereof.

Possible sulfone dyes are all sulfone dyes known to one of skill in the art for detection purposes. Specific examples of sulfone dyes include, but are not limited to, aliphatic and aromatic sulfonic acids such as alkylbenzenesulfonic acids and alkylbenzenesulfonates, Brilliant Blue FCF (i.e., erioglaucine), azorubine and naphthalenesulfonic acid, or combinations of at least two thereof.

In some instances, the diffusable label can be erioglaucine, indigo carmine, hydroxynaphthol blue, 1,1-diethyl-4,4-carbocyanine iodide or amaranth. Erioglaucine absorbs light of a wavelength of about 625 nm, indigo carmine absorbs light of a wavelength of about 608 nm, thydroxynaphthol blue absorbs light of a wavelength of about 650 nm, 1,1-diethyl-4,4-carbocyanine iodide absorbs light of a wavelength of about 703 nm or about 648 nm, and amaranth absorbs light of a wavelength of about 521 nm. In other instances, the diffusable label is erioglaucine, hydroxynaphthol blue, or a combination thereof.

These dyes generally have a diffusion behavior that is virtually independent of the presence or the concentration of the analyte. Conversely, the diffusable label should influence the behavior of the analyte as little as possible. However, it is also possible to use other dyes that exhibit a dependence of their diffusion rate in a sample on the temperature or on particulate or cellular constituents (e.g., Hct). A list of the structural formulae relating to the aforementioned dyes and the absorption maximum thereof can be found in Table 1 in the experimental section.

The diffusable label can be further configured so that it interacts with the analyte and/or with the test chemistry as little as possible or not at all, where a diffusion rate of the label is substantially independent of the concentration of the analyte. What ought to be achieved is that the detection reaction proceeds undisturbed by the diffusable label and the diffusion of the label in each case. Thus, the diffusion rate of the diffusable label is substantially independent of the concentration of the analyte. For example, chemical reactions or other interactions between, firstly, diffusable label, and, secondly, analyte or test chemistry are generally undesired. The interaction between, firstly, diffusable label and, secondly, analyte and test chemistry ought to be so low that the signals obtained using analyte and test chemistry without the diffusable label deviate by less than about 3%, by less than about 2% or by less than about 1% from signals obtained from measurements with analyte and test chemistry in the presence of the diffusable label.

To keep an interaction between the diffusable label and the analyte as low as possible, the diffusable label can be situated in a region which, while coming into contact with the sample to be analyzed, does not come into contact with the test chemistry.

In some instances, the diffusable label can be arranged completely or partly separately from the test chemistry. The label can be arranged completely or partly separately from the test chemistry at least before wetting of the test element and/or of the diffusable label with sample. In this manner, the diffusable label is prevented from being influenced by the test chemistry and the test chemistry is prevented from being influenced by the diffusable label, at least during the wetting process. The separation of the diffusable label from the test chemistry can be achieved by a separate test field or by a separate test field layer with the diffusable label but without test chemistry or detection reagent being arranged on the test element. Alternatively or additionally, it is possible to use a distinct test element containing the diffusable label, which test element, while being wetted with the same sample at the same time and under the same temperature conditions, does not contain any detection reagents. Alternatively or additionally, an influence on the diffusion rate of the diffusable label by the analyte can be determined experimentally beforehand, and this can be taken into account in the concentration calculation method described in more detail below. In other instances, the diffusable label and the test chemistry are arranged in the same test field.

The test elements have two opposite surfaces. As such, the analyte detector and/or the diffusable label detector therefore can irradiate the test elements or a part thereof from one side (i.e., a detection side) with light. Reflected or scattered light emanating from the test elements can be detected from an opposite side from the detection side by using the photosensitive detector element of the diffusable label detector and/or the photosensitive detector element of the analyte detector.

Such test elements can be wetted with the sample from the opposite side, which can also be referred to as a sample input side or application side and which can face the detection side. For example, the test elements can include at least one sample input/application side and at least one detection side. Alternatively or additionally, the sample can be applied at another site such as, for example, at a capillary element of the test element.

The test elements also can have two spatially separate regions for detecting the analyte and for detecting the diffusable label. For example, two adjacent regions of the test elements can be arranged in relation to one another so that they both can be contacted with the sample but no fluid exchange is possible between them (i.e., no diffusion is possible from one region to the other). Alternatively, the regions for detecting the analyte and for detecting the diffusable label can be arranged next to one another, and in each case diffusion of the analyte and/or diffusion of the label shall be possible. As such, these two regions can be arranged in relation to one another so that when introduced into a measurement instrument, they can be illuminated by a light source in each case. The region in which the diffusable label is situated alternatively can be formed as a capillary, which is filled upon wetting with the sample. For detecting the diffusable label, a diffusion of the label in the capillary can be determined.

The test elements also can include at least one partition layer that retains at least one constituent of the sample such as, for example, particulate and/or cellular constituents including red blood cells, white blood cells and/or platelets. Alternatively or additionally, the at least one partition layer can include at least one optical material such as, for example, at least one pigment for forming a reflection layer in the form of a pigment layer. Examples of optical material include, but are not limited to, $TiO_2$, $ZrO_2$ or $BaSO_4$. In some instances, the partition layer is situated on the test field. More specifically, the partition layer can be situated on the side of the test element on which the sample is applied (i.e., the sample input side). For example, the sample can be applied on the side of the test element having the partition layer, whereas the detection of the analyte can be achieved optically on the opposite side. During penetration of the sample into the test element, the sample or parts of the sample can penetrate one or more layers of the test field such as the partition layer and come into contact during the penetrating with both the test chemistry and optionally the diffusable label. In addition, part of the sample can remain in or above the partition layer as a supernatant or part of a supernatant.

The test elements therefore can have at least one label layer and/or at least one label field that includes the at least one diffusable label. As used herein, "layer" or "field" means a cohesive quantity of the particular material, which quantity has a lateral extent and a thickness. For example, the layer and/or the field can have a lateral extent such as a diameter and/or an equivalent diameter and/or a side length of at least about 100 µm, at least about 500 µm or at least about 1 mm. In addition, the layer and/or the field can have a thickness of less than about 100 µm or even less than about 50 µm. A layer can be a component of a multilayered assembly. The field can have an accessible surface that can be contacted with a liquid sample. Alternatively, the field can be covered by one or more further layers and/or elements.

The test elements also can have one or more test fields that include the at least one test chemistry. Thus, the at least one label can be completely or partly contained in the at least one test field or be completely or partly mixed into the at least one test chemistry and/or be contained in another way in the test field. In some instances, the at least one label can be arranged completely or partly separately from the test chemistry, but on the same test element and the same test support. As used herein, "separately" means that the test chemistry and the label are not contained in a common, cohesive material, for example, not in the same layer and/or not in the same layer assembly. The diffusable label can be arranged in particular in at least one label layer at least before wetting with the sample, which label layer is arranged adjacent to or spaced apart from the test chemistry layer on adjacent or spaced-apart areas on a test support of the test element. The areas can be spaced apart by at least about 100 µm, by at least about 200 µm or by at least about 500 µm. Alternatively or additionally, the at least one label layer can be arranged separated from the test chemistry layer by one or more layers in a layer assembly including at least one test chemistry layer and at least one label layer different from the test chemistry layer. In this manner, the label layer and the test chemistry layer can directly adjoin to one another, or one or more further layers can be arranged between the label layer and the test chemistry layer. Alternatively, the diffusable label can be arranged in at least one label layer above and/or below the test field. The label layer can be a component of the test element (e.g., the test field), but also can be a layer separate from the test element, which layer is nevertheless wetted by the same sample. Alternatively, although the label layer can be arranged on the test element, it is not a component of the test field. By separating the label from the test chemistry, it can be ensured that the label does not influence the diffusion properties and reaction properties of the test chemistry. Again alternatively or additionally, the label and/or the label layer can be completely or partly arranged outside the test element, for example in a separate correction element and/or in a device for determining at least one concentration of at least one analyte in a sample, for example a test instrument.

Methods

Methods of the inventive concept include a step of performing a calibration measurement to obtain at least one piece of correction information. Thus, at least one calibration measurement is acquired, which can be a general relationship between at least one interfering variable and diffusion of the diffusable label. The general relationship can be reported in the form of one or more calibration curves. As used herein, "general relationship" means a rule for a plurality of different values of the interfering variable, which rule describes how the values of the interfering variable influence the diffusion of the diffusable label. The rule can be ascertained for a continuous range of values of the interfering variable or for a discontinuous range of values such as, for example, a quantity of interfering variable values spaced apart from one another. Accordingly, the general relationship can include a pointwise assignment of multiple interfering variable values to, in each case, a corresponding influence on label diffusion. Alternatively or additionally, the rule can be a law in the form of an analytical function, which can be referred to as a calibration curve or calibration function and which describes analytically the influence on label diffusion by the interfering variable.

In some instances, the calibration measurement can be carried out by detecting, in each case, at least one diffusion of at least one diffusable label in a plurality of test samples or calibration samples in which the interfering variable is known. For example, it is possible to prepare test samples having a known Hct and/or temperature. With respect to such test samples, it is possible in each case to ascertain at least one value of a diffusion of the diffusable label. As explained in more detail below, it is possible to ascertain with respect to each test sample at least one optical measurement value (e.g., at least one reflectance value) of a label field in contact with the test sample. In this manner, it is possible to determine a quantity of pairs of values, which each include the interfering variable and the associated diffusion of diffusable label. The pairs of values can themselves describe the general relationship, or the general relationship can be ascertained from the pairs of values by means of a fit. In some instances, it is possible for the general relationship to be described by a straight line, where the slope and axis intercept can be readily determined from the pairs of values by an appropriate fit. The straight line then can be used as a calibration curve. More complex calibration curves also are possible such as, for example, exponential functions and/or polynomials that describe the relationship between the pairs of values.

The general relationship, more particularly the calibration curve or calibration function, can be stored in at least one data storage device such as, for example, a volatile and/or non-volatile data storage device of the devices described above such as, for example, an evaluation unit of the device as describe above.

As noted above, and as part of the inventive concept, the methods use at least one diffusable label. As noted above, in some instances, diffusion of the diffusable label from at least one first region into at least one second region can be detected. The first and/or second region can each be regions of the test element. It is clear that there are a multiplicity of options for detecting diffusion by a change in concentration being observed locally.

As such, diffusion of the at least one diffusable label in the sample or at least one constituent thereof can be caused by differences in concentration of the diffusable label such as, for example, between the first and second region. As a result of wetting of the test element and/or of the diffusable label, a difference in concentration can arise between at least one first region, in which the label is situated before wetting, and at least one second region such as, for example, a supernatant of the sample and/or a region of the test element and/or of a correction element different from the first region, and so the label diffuses owing to the difference in concentration.

The diffusion of the diffusable label can be detected electrochemically or optically. For example, one or more diffusable label detectors can be used that can be configured to detect the diffusion of the diffusable label.

Moreover, a concentration of the diffusable label in at least one observation volume in the first region and/or the second region can be acquired at at least two different times or at multiple times. For example, a particular volume in which the diffusable label is situated before wetting with sample can be measured electrochemically and/or optically. After wetting of the volume and other volumes of the test field, the concentration of the diffusable label in the volume will sink owing to the differences in label concentration. Alternatively or additionally, it is possible to observe a particular volume that builds up with the diffusable label after wetting with sample.

The diffusion rate of the diffusable label generally depends on many different parameters, such as, for example, temperature, pressure and the chemical environment of the diffusable label. As used herein, "chemical environment of the label" means the environment of the label before wetting with sample and/or the environment of the diffusable label after wetting with sample. Since the chemical environment of the diffusable label should be known before wetting with sample, the diffusion rate of the diffusable label after wetting is influenced mainly by the constituents of the sample and the temperature, especially when it is assumed that operations are carried out at approximately normal pressure.

Advantageously, diffusion of the diffusable label before wetting with sample is negligible, since the label is situated in an at least virtually dry environment in which there are no, or merely negligible, diffusion processes. For example, at least one first detector signal for determining a diffusable label concentration before wetting and at least one second detector signal for determining a diffusable label concentration after wetting across a particular period and/or at a particular time, can be used as a basis for detecting a diffusion of the diffusable label, after wetting of the label with sample in the form of a diffusion rate of the diffusable label. Alternatively or additionally, it is also possible to observe a period only after wetting of the diffusable label. Further alternatively or additionally, a detection signal can be effected at a particular time after wetting of the label with sample. In some instances, the diffusion of the diffusable label depends on only few, previously known parameters. For example, the diffusion rate of the diffusable label used in a glucose determination should not depend on the concentration of the analyte to be determined, in this case glucose.

The piece of correction information thus includes at least one piece of information about at least one interfering variable of the sample. For example, the interfering variable can, as explained above, be a Hct and/or a temperature of the sample or a combination thereof. Other interfering variables also are correctable.

If one or more detector signals are used for detecting diffusion of the diffusable label, the detector signal(s) can be compared with one or more reference curves that are characteristic of various temperature and concentration relationships of the sample. From this, it is possible to directly or indirectly determine the temperature and/or at least one other parameter of the sample. Alternatively or additionally, it is possible, at different times after wetting of the diffusable label with the sample, to detect concentrations of the diffusable label and to compare them with stored reference curves. Alternatively or additionally, it is possible, within particular time ranges after the wetting of the label with sample, to ascertain rises in the detector signal, which can likewise be compared with reference curves. In this manner, it is possible to determine both the temperature-dependent influence of the diffusion rate of the diffusable label, and the influence of the diffusion rate of the diffusable label owing to the chemical composition of the sample.

As noted above, detecting the diffusable label can be carried out with the same detector for detecting the analyte. The at least one detector should be able to carry out an optical detection at multiple wavelengths. Alternatively, it is possible to use a combined detector that has two detector units that can detect at different wavelengths. If different detectors are used for the analyte detection and diffusable label detection (e.g., at least one analyte detector and at least one label detector, for example at least one optical analyte detector and at least one optical label detector, the detectors can be arranged in different ways. For example, the detectors can be arranged on sides of the test element that oppose one other (e.g. the analyte detector on the detection side and the label detector on the sample input side). Alternatively or additionally, the detectors can be completely or partly arranged on the same side of the test element (e.g., on the detection side). In addition, filters can be used in the beam path between light source and detector. Filters generally are able to filter out one or more wavelengths of the light by absorbing or reflecting them.

The methods also include a step of detecting an analyte of interest in a body fluid sample with a test element as disclosed herein. As used herein, "detection of a reaction of the test chemistry with the analyte" means a process in which the reaction itself and/or one or more reactants involved in the reaction and/or one or more reaction products are acquired qualitatively or quantitatively by qualitative and/or quantitative acquisition of at least one change in property of the sample and/or of the test chemistry and/or of at least one further element or range which is influenced by the detection reaction. For example, the reaction of the test chemistry with the analyte can be detected by means of electrochemical and/or optical detection methods. Such detection methods, which can be carried out using at least one detector are known to one of skill in the art.

In some instance, the body fluid sample is blood or a constituent thereof.

Thus, it is possible to ascertain at least one optical measurement value, such as at least one reflectance value, which detects the reaction of the test chemistry with the analyte. As noted above, it is possible to ascertain at least one optical measurement value (e.g., at least one further reflectance value), which detects the diffusion of the diffusable label. As such, optical measurement values for detecting the reaction of the test chemistry with the analyte and for detecting the diffusion of label can be acquired in particular at different wavelengths.

Optically detecting the analyte can be achieved by using a detector having at least one optical sensor configured to receive light and to generate at least one corresponding signal. In addition, at least one light source can be used to illuminate the test element and/or a part thereof and/or the sample and/or a part thereof and/or an optional correction element and/or a part thereof, the optical sensor being used to detect reflected and/or scattered and/or emitted light. When optically detecting the analyte and/or diffusable label, it is advantageous when the wavelengths of the incident light and/or of the detected light are distinctly different so that a distinction between the two signals can be made. As used herein, "distinctly different" means a deviation of the wavelengths to be detected for analyte determination with respect to the wavelength to be detected for determining the label of at least about 20 nm, of at least about 30 nm, or of at least about 50 nm.

In some instances, the analyte is determined at a different wavelength with respect to the diffusable label. In this manner, the diffusable label detector can have at least one diffusable label detector light source, and the analyte detector can have at least one analyte detector light source, it being possible to configure the label detector light source to illuminate the test element with light of a different wavelength with respect to the analyte detector light source. For example, the light of the diffusable label detector light source can have a shorter wavelength than the light of the analyte detector light source or vice versa. Specifically, the analyte can be detected with the aid of light within a wavelength range from about 400 nm to about 1000 nm, from about 500 nm to about 800 nm, from about 640 nm to about 680 nm, or about 660 nm. In this connection, the label can be detected with light within a wavelength range from <about 400 nm, from about 300 nm to <about 400 nm, or at about 360 nm.

An inverse design is also possible. That is, the diffusable label can be detected with the aid of light within a wavelength range from about 400 nm to about 1000 nm, from about 500 nm to about 800 nm, from about 640 nm to about 680 nm, or at about 660 nm. In this connection, the analyte can be detected with light within a wavelength range from <about 400 nm, from about 300 nm to <400 nm, or at about 360 nm.

In some instances, the diffusable label absorbs light within a wavelength range from about 400 nm to about 800 nm. The diffusable label, which can be in the form of a dye, can be excited with the aid of light having a wavelength within a wavelength range from about 300 nm to about 800 nm (but preferably less than 400 nm) or absorb light within the wavelength range, or from about 300 nm to about 500 nm, or from about 340 nm to about 380 nm.

In other instances, an inverse design can be used in which a different light source is used in each case for analyte determination and diffusable label determination. For example, two different LEDs can be used. The LED for exciting the analyte can have an intensity maximum around about 660 nm, whereas the LED for exciting the diffusable label can have an intensity maximum around about 360 nm. Alternatively, it is also possible to use a light source having light that is processed with the aid of optical means, such as filters, apertures or mirrors, so that the detection region is irradiated with light of different wavelengths at different times. In some instances, the wavelength range of the light for detecting the diffusable label is at least about 5 nm, at least about 10 nm, at least about 50 nm, or at least about 100 nm away from the wavelength range of the light for detecting the analyte. This can be realized in various ways. Alternatively, the wavelength range of the light for detecting the diffusable label is within a range from about 5 nm to about 100 nm away from the wavelength range of the light for detecting the analyte.

To determine the interval between the wavelength ranges for detecting the diffusable label and the analyte, one can consider the interval between the absorption maximum of the diffusable label and of the analyte. For example, it is possible to use two light sources having different wavelength ranges of the emitted light. In addition, it is possible to use only one light source having a broad wavelength range of the emitted light, it being possible to use filters in the beam path with the result of using the filters being that the determination of the label is carried out at a different wavelength with respect to the determination of the analyte.

In some instances, the methods use not only at least one first diffusable label but also at least one further diffusable label different from the first diffusable label, where the diffusion rate of the first diffusable label and the diffusion rate of the at least one further diffusable label are influenced by at least one first property of the sample and by at least one further property of the sample different from the first property, respectively. By using more than one diffusable label, it is possible to determine possible influences on the diffusable label by different properties of the sample. The first diffusable label can be erioglaucine, indigo carmine, hydroxynaphthol blue, 1,1-diethyl-4,4-carbocyanine iodide and amaranth and can be used to ascertain an influence of a first property of the sample on the diffusion rate of the diffusable label. For example, the first property of the sample can be a temperature of the wetted test field and/or of the sample, or a Hct of the sample to generate at least one first piece of correction information. Likewise, the at least one further diffusable label can be erioglaucine, indigo carmine, hydroxynaphthol blue, 1,1-diethyl-4,4-carbocyanine iodide and amaranth and can be used to determine at least one further property of the sample, such as, for example, temperature or Hct of the sample to generate at least one second piece of correction information. In some instances, use is made of a combination of a first diffusable label such as a sulfone dye for determining the influence of temperature on the diffusion rate and a further diffusable label such as an azo dye for determining a further influence of Hct of the sample on the diffusion rate. In other instances, a single label such as a sulfone dye is sufficient for determining the influence of a first and at least one further property such as temperature and Hct of the sample on the diffusion rate of the label.

By using more than one diffusable label, however, an increased accuracy of the test method can be made possible. For example, two different diffusable labels can be used, where one of the labels exhibits a dependence of the diffusion rate on the basis of temperature but only a slight dependence of the diffusion rate on the basis of Hct, and where a second diffusable exhibits a dependence of the diffusion rate on the basis of Hct but only a slight dependence of the diffusion rate on the basis of temperature. It is thus possible to gain more accurate pieces of correction information for determining the concentration of the analyte. It also is possible to use different diffusable labels having different spectral properties (e.g., dyes that absorb differently).

In some instances, the reaction of the test chemistry with the analyte is detected by means of at least one first detector, which can be referred to as an analyte detector. Specifically, the analyte detector can include at least one first photosensitive detector element such as at least one first photodiode. In addition, the analyte detector can include at least one analyte detector light source such as at least one first LED.

The diffusion of the diffusable label can be detected by means of at least one second detector, which can be referred to as a diffusable label detector or diffusion detector. Specifically, the label detector can include at least one second photosensitive detector element such as at least one second photodiode. In addition, the label detector can include at least one label detector light source such as at least one second LED. As noted above, the first detector and the second detector can be formed separately or can also be at least partly identical. More particularly, the analyte detector light source and the label detector light source can be formed differently, whereas the first photosensitive detector element and the second photosensitive detector element can be designed to be identical in terms of components. For example, the detection side of the test element can be provided with the analyte detector light source and the label detector light source for illuminating the test element or parts thereof, and also with a common photosensitive detector element such as a common photodiode, which alternately receives reflected light of the label detector light source and of the analyte detector light source. Other designs are also conceivable in which different photosensitive detector elements are used.

As noted above, the analyte and/or the diffusable label can in each case be independently detected electrochemically and/or optically. If, for example, the analyte is to be analyzed electrochemically and the diffusable label optically, or the analyte optically and the diffusable label electrochemically, both at least one electrochemical and at least one optical detector is generally necessary. Alternatively, both the analyte and the diffusable label can be detected optically and/or electrochemically. To this end, two different detectors can be used, and this is especially advantageous when the wavelength ranges for ascertaining the analyte concentration are very different from the wavelength ranges for ascertaining the label concentration. However, it also is possible to use one detector that provides the possibility of detecting light at more than one wavelength. If the analyte and diffusable label are not situated within a common test chemistry layer, it may be advantageous to perform the detection of the analyte and of the diffusable label from different sides of the test element. To this end, detecting the analyte would advantageously be carried out on the side facing away from the sample input side, whereas detecting the diffusable label can take place outside the test element such as, for example, in a region of the test field closer to the sample input side. Alternatively, it is possible to use one or two detectors in the event that the diffusable label is not situated on or in the same test field as the detection reagents. For example, one detector can cover the area of two test fields or two test elements. In this manner, the regions containing diffusable label can be illuminated with light of a different wavelength with respect to the regions containing no label.

The concentration of the diffusable label and/or of the detection reagent can be detected either directly or indirectly. In the case of a direct detection, use is made of a method that immediately qualitatively and/or quantitatively detects the presence of the substance to be detected, in this case the label or the detection reagent for the analyte. In contrast, and in the case of an indirect detection, the presence of the at least one diffusable label or of the one detection reagent is qualitatively and/or quantitatively inferred via at least one conceptual, theoretical or experimental intermediate step. For example, this can be done via the presence and/or formation and/or decrease of one or more further substances, it being possible in turn to qualitatively and/or quantitatively infer the label or analyte, and so the label or analyte can be detected indirectly. A known example of such a detection reagent for the detection of blood glucose is nicotinamide adenine dinucleotide (NADH) (i.e., the reduced form of nicotinamide adenine dinucleotide ($NAD^+$)), which can be directly detected photometrically. Altogether, for the design of possible labels or detection reagents and test fields, reference can, however, be largely made to the art.

As used herein, "conversion" means a reaction in which the analyte is involved and/or is chemically modified. In this manner, the test chemistry can ensure the specificity of the test element. For example, the detection can be achieved via a test chemistry containing an enzyme and a coenzyme by, for example, redox equivalents transferred by the analyte through the coenzyme by a mediator, such as manganese dioxide. The redox equivalent can be converted for photometric and/or optical concentration measurements of the analyte with an indicator.

In some instances, the reaction of the test chemistry with the analyte is detected by means of at least one first detector, where diffusion of the diffusable label is detected by means of at least one further detector such as at least one second detector.

As explained above, the methods generate at least one piece of correction information from the diffusion of the diffusable label. The methods therefore also include a step of correcting the analyte concentration measurement with the at least one piece of correction information that was obtained by detecting diffusion of the diffusable label in the actual sample and from the general relationship between the interfering variable and the diffusion of the label. This can be achieved in a simple manner by using the detected diffusion of the label in the actual sample (e.g., the optical measurement value of the label and, more particularly, the reflectance of the label field), as a function value of the general relationship as a function value of the calibration curve or calibration function, producing the piece of correction information.

The thus ascertained piece of correction information can then be used for correcting the analyte concentration and/or for correction of the detection of the reaction of the test chemistry with the analyte. For example, in the sample in which the analyte concentration is to be determined, at least one uncorrected optical measurement value, for example a reflectance, can be initially acquired, which is subsequently corrected with the piece of correction information in order to obtain a corrected optical measurement value. The correction can, for example, be achieved by addition or subtraction of the piece of correction information from the uncorrected optical measurement value and/or by multiplication of the piece of correction information with the uncorrected optical measurement value and/or by formation of a linear combination from the piece of correction information and the uncorrected optical measurement value.

For example, the piece of information can be a piece of information about how at least one measurement value such as, for example, an electrochemical and/or optical measurement value, is to be converted into an analyte concentration. For example, the piece of correction information can include a piece of information about which conversion rule is to be applied when converting the at least one measurement value into the analyte concentration and/or how a conversion rule is to be designed and/or modified. As such, multiple pieces of correction information corresponding to detected diffusion of the label can be stored in a data processing device and/or in a data storage device.

Alternatively or additionally, it is possible to store at least one assignment rule which can be generated analytically, empirically or semi-empirically, which assigns to each acquired diffusion a piece of correction information for determining the analyte concentration. For example, the piece of correction information can be generated by comparing a detector signal of a diffusable label concentration determination with stored reference curves, by it being possible to assign a profile of the detector signal to a particular reference curve, which is in turn characteristic of a particular temperature and/or of a particular Hct.

It is possible for further pieces of correction information to be determined through determining the diffusable label concentration. For example, it is possible to ascertain a moistness of the test element before wetting with sample by comparing a detector signal for the label concentration before wetting with a reference value.

EXAMPLES

The inventive concept will be more fully understood upon consideration of the following non-limiting examples, which are offered for purposes of illustration, not limitation.

Example 1: Methods and Materials

Figure 1D:
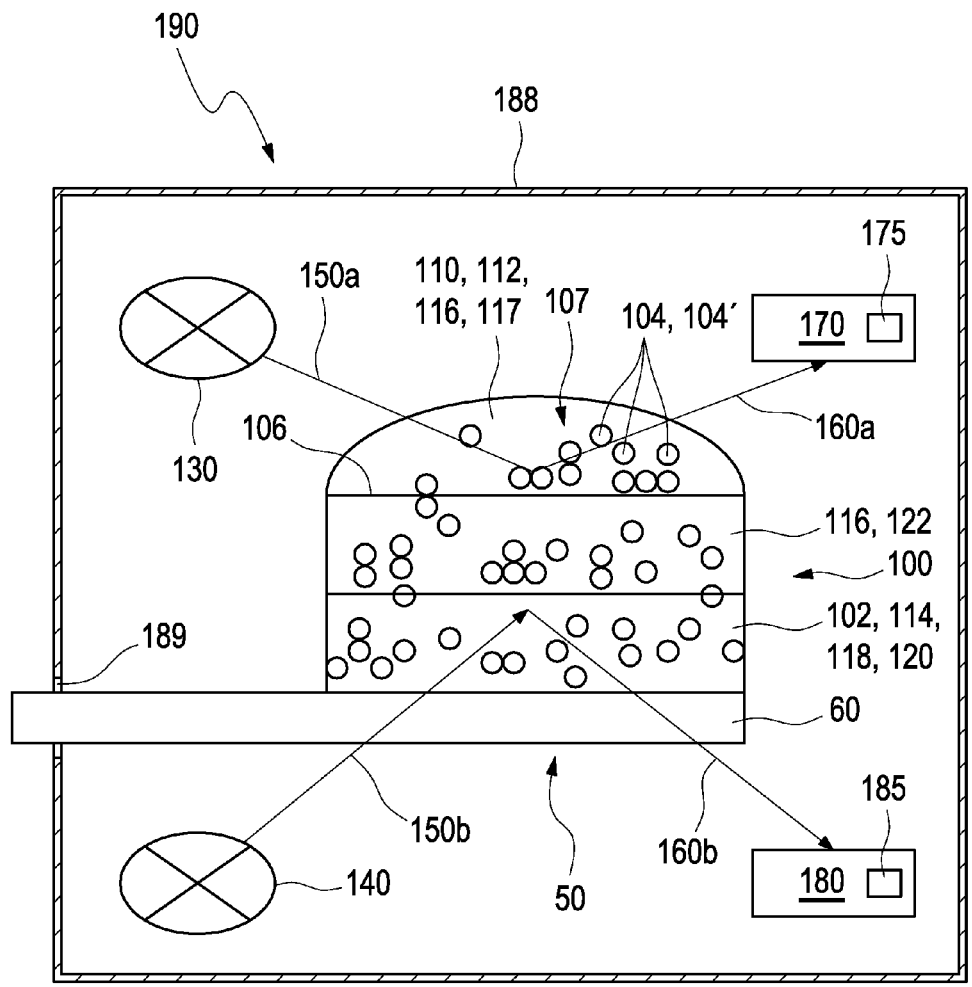
FIG. 1d shows a diagram of an exemplary device having an exemplary test element.

FIG. 1a shows an exemplary test element 50 for detecting at least one analyte 117 in a sample 110, on which a test field 100 is arranged on a test support 60. The test element 50 is configured to be used in a device 190 as shown in FIG. 1d. The test field 100 includes a test chemistry 102 of one or more detection reagents, such as an enzyme that converts the analyte 117 and thus makes it possible to infer an analyte concentration. In addition to the test chemistry 102, at least one diffusable label 104, 104' also can be situated in or on the test field 100; however, the diffusable label 104, 104' can be situated on a separate test element 50 or on another site on the test support 60 of the test element 50. The diffusable label 104, 104' can be arranged together with the test chemistry 102 and, in this way, form at least one test chemistry layer 118. The test chemistry layer 118 also is known as a reactive layer owing to its reactivity. Alternatively, the diffusable label 104, 104' can be arranged in a separate layer and form a separate label layer 120, as shown in FIGS. 1b and 1c.

Situated adjacent thereto is a pigment layer 122. The pigment layer 122 can be at a distance from the test chemistry layer 118. Introduced in the pigment layer 122 is, for example, a pigment such as $TiO_2$ or $ZrO_2$. In an optical detection, the pigment layer 122 serves, as shown in FIG. 1d, to reflect the incident light 150b that penetrates through both the test support 60 and the reactive layer 118. This ensures that the light 150b of the light source 140, while being able to interact with the detection reagents in the reactive or test chemistry layer 118, is not influenced by other constituents of the blood 110. These interfering constituents, such as red blood cells, can be kept away from the reactive layer 118 by a partition layer 106.

FIGS. 1b and 1c each show a test field 100 on a test support 60 of a test element 50, as can be measured in the device 190 of FIG. 1d. The test field 100 in FIG. 1b shows the state of the test field 100 before wetting 108 with a sample 110. In contrast, the test field 100 in FIG. 1c shows the state after wetting 108 of the test field 100 with sample 110. In this connection, the sample 110 may be blood.

The diffusable label 104, 104' can be situated in a first region 114 of the test field 100, in which the test chemistry 102 may likewise be situated. Alternatively, the test chemistry 102 can be accommodated in a separate layer 118 or in a second region 116 of the test field 100. If the diffusable label 104, 104' is accommodated in a separate layer 120, this is known as a label layer 120, from which the test chemistry layer or reactive layer 118 is distinguished separately. If diffusable label 104, 104' and test chemistry 102 are accommodated in the same layer, this is known only as a test chemistry layer 118, 120.

In FIGS. 1a-c, one or more further layers (not shown) can be present above, between or below the two layers 118 and 120. Furthermore, further additives such as pigments, fillers, auxiliaries and other substances can be present in both the test chemistry layer 118 and the label layer 120, giving rise to a pigment layer 122. Alternatively, the additional substances can be present in only one or in more than one of layers 118, 120.

As shown in FIGS. 1b-c, the diffusable label 104, 104' spreads after wetting 108 with sample 110 from the first region 114 of the test field 100, in this case the test chemistry layer 118, into at least one second region 116. The second region 116 can be situated directly adjacent to the first region 114 or be at a distance from the first region 114. In some instances, the diffusable label 104, 104' can diffuse through all layers of the test field 100. The second region 116 also can be the supernatant 112 of the blood 110 that has not been taken up by the test field 100 and that has accumulated on the sample input side 107. Alternatively or additionally, the second region 116, into which the diffusable label 104, 104' diffuses after contact with the sample 110 and can be detected, can be outside the test element 50. Further layers can be situated between the first 114 and second region 116, such as the partition layer 106. Alternatively or additionally, the second region 116 can be a component of the test element 50 and/or test field 100.

For detecting the diffusable label 104, 104', one or both of regions 114 and/or 116 can be used. If the first region 114 is used, "bleeding" of diffusable label 104, 104' from the first region 114 is detected by optical or electrochemical means. As used herein, "bleeding" means a diffusion of the diffusable label 104, 104' from the first region 114. Depending on the diffusable label 104, 104' used, this can lead to an increase or decrease in the measurement signal. Alternatively, the inward diffusion of diffusable label 104, 104' can be detected in part of or the entire second region 116.

The measurement signal increases or decreases during the diffusion process depending on whether the diffusable label is an absorption dye whose reflection 160a of incident light 150a is detected or is a fluorescent dye whose conversion of the incident light to another wavelength is detected. Conversely, the measurement signal will decrease or increase when detecting the absorption dye or fluorescent dye takes place in the second region 116. Alternatively, both regions 114 and 116 can be used for detecting diffusion of diffusable label 104, 104'.

As an alternative to optically detecting diffusion of diffusable label 104, 104', the diffusable label can be electrochemically detected. To this end, an electrode accommodated in the first region 114 would detect the bleeding of the first region 114 of diffusable label 104, 104' after wetting 108.

FIG. 1d shows a device 190 having two light sources 130 and 140 within a housing 188, each on one side of a test element 50 inserted into the housing. In the device 190, light 150*a* can be irradiated from a first light source 130 onto the upper side of a test element 50 to be measured in the device 190. The light 150*a* emanating from the first light source 130 strikes the surface of the test field 100 of the test element 50 and is reflected there. The light beam 160*a* reflected on the test field 100 is collected by a first detector 170. On the route from the first light source 130 up to the first detector 170, the light 150*a* moves to some extent through the sample 110 and/or the supernatant of the sample 112, which supernatant can simultaneously represent a second region 116 of the device 190. In the process, light 150*a*, 160*a* can strike diffusable label 104, 104', which has diffused from the first region 114 into the second region 116 after wetting 108 with sample 110 and now absorbs some of the incident light 150*a* and/or reflected light 160*a*.

Alternatively or additionally, the bleeding of diffusable label 104, 104' after wetting 108 of the test field 100 can be detected with a second detector 180. This can be performed when diffusable label 104, 104' is introduced together with the test chemistry 102 in the test chemistry or reactivity layer 118. To this end, on the underside of the test element 50, opposite the sample input side 107, light 150*b* from a second light source 140 is irradiated through the test support 60 and the test chemistry 102 in the test chemistry or reactive layer 118 and reflected on the pigment layer 122. Light 160*b* from the second light source 140 is reflected on the pigment layer 122 and is collected by the second detector 180. In this way, it is possible to detect both the light for the detection reaction, which makes it possible to infer the converted quantity of the analyte 117, and the light influenced by diffusable label 104, 104' or the influenced radiation, which reflects the diffusion of diffusable label 104, 104'.

If light source 140 and detector 180 are designed to emit or detect both light at the corresponding wavelength for detecting the detection reagent of the test chemistry 102 and light at the corresponding wavelength for detecting diffusable label 104, 104', one light source 140 and one detector 180 can be sufficient for observing both the detection reaction of the analyte 117, and the diffusion of diffusable label after wetting 108 of the test field 100.

Additionally, evaluation units 175 and/or 185 can be situated in or adjacent to detectors 170 and/or 180, which compare the signal with reference curves or reference values stored therein.

The detectors 170 and 180 used can be photodiodes, charge-coupled device CCD) sensors or complementary metal-oxide semiconductor (CMOS) sensors. Light sources 130 and/or 140 can be LEDs, mercury lamps or other light sources having the desired wavelengths. As noted above, evaluation unit 175 and/or 185 can be situated adjacently in or on detectors 170 and/or 180. Evaluation unit 175 and/or 185 can be a microprocessor or another suitable calculator unit. However, it is possible for merely a storage device to be situated in the detector, which storage device can transfer data to an external evaluation unit (not shown here) or be read thereby.

Following the measurement, the test element 50 can be taken out again from the housing 188 so that a further test element 50 can be inserted for a further measurement. The housing 188 serves especially as protection for the electronic components within the housing 188, such as detectors 170 and/or 180 with evaluation unit 175 and/or 185 and also light sources 130 and/or 140. However, housing 188 also serves as protection for the user to prevent maloperation. The housing 188 has an opening 189 so that the test element 50 having the test field 100 can be inserted into the housing 188.

As an alternative to the arrangement of diffusable label 104, 104' within a restricted region of the test field 100, as shown in FIG. 1*b*, it is possible for diffusable label 104, 104' to be situated within the entire test field 100 of the test element 50, making it possible to detect bleeding of the test field 100 of diffusable label 104, 104' with the supernatant 112 serving as second region 116 following wetting 108 of the test field 100.

An alternative arrangement of test chemistry 102 and diffusable label 104, 104' is shown in FIGS. 1*e-f*. A test element 50 is shown that has a test support 60 on which a test field 100 is arranged and in which a label layer 120 and a reactive layer 118 are arranged next to one another. Situated in the label layer 120 is diffusable label 104, 104', which can be optionally separated from the reactive layer 118 by a barrier 101. In some instances, however, the test element 50 does not have a barrier 101 between label layer 120 and reactive layer 118. The result of using the optional barrier 101 can be that before and/or after wetting of the test field 100 with sample 110, hardly any substance exchange takes place between label layer 120 and reactive layer 118. After wetting of the test field 100, it is usually acceptable that a substance exchange by diffusion can take place. The result of using this arrangement of the label layer 120 next to the reactive layer 118 is that these two layers can be independently illuminated by, in each case, light source 130 and 140. For example, the label layer 120 is illuminated by incident light 150*a* of the first light source 130, and the reactive layer 118 is illuminated by incident light 150*b* of the second light source 140. The label layer 120 and the reactive layer 118 can have an identical or non-identical volume and/or an identical or non-identical layer thickness. FIG. 1*e* shows a design in which the reactive layer 118 and the label layer 120 differ in layer thickness, whereas FIG. 1*f* shows a design in which the reactive layer 118 and the label layer 120 are substantially identical in layer thickness. In some instances, the label layer 120 and the reactive layer 118 are substantially identical in layer thickness and/or are substantially identical in volume. As used herein, "substantially identical" means identicalness or else a deviation of the layer thicknesses or of the volumes from one another by not more than about 20%, by not more than about 10%, or by not more than about 5%.

After wetting of the test field 100 with the sample 110, diffusable label 104, 104' can diffuse from the first region 114, such as at least part of the label layer 120, into the second region 116. The second region 116 can include the supernatant 112 of sample 110 and/or a further layer 116 above and/or lateral to (not shown here) the label layer 120. If the barrier 101 is designed so that it is permeable to diffusable label 104, 104', the reactive layer 118 can serve as at least part of the second region 116 into which diffusable label 104, 104 can diffuse after wetting. Conversely, part of the analyte to be detected can be situated in both the supernatant 112 and the second region 116.

In some instances, the region into which diffusable label 104, 104' can diffuse and the region into which the analyte 117 can diffuse are about the same size. In FIG. 1*e*, the proportions of the layers 116 and 118 are not necessarily portrayed true-to-scale for all conceivable embodiments having label layer 120 and reactive layer 118 arranged next to one another. For instance, the second region 116 together with the first region 114 or the label layer 120 can have the same layer thickness and/or the same volume as the reactive layer 118. However, alternative designs also are contemplated. For example, in one alternative design, the label layer 120 can by itself have the same layer thickness and/or the same volume as the reactive layer 118 (see, FIG. 1f). Likewise, and for detecting reflected light in the form of the reflected light of the first light source 160a and of the second light source 160b, detector 170 can be used. Additionally, it is possible to use a further detector, thus making it possible to collect the reflected light beams 150b and 160b separately.

FIGS. 2-9 show curve profiles or kinetics for the outward flow of various diffusable labels (e.g., dyes) from a label layer and test chemistry layer 118, 120 in a conventional test field 100 into the supernatant of sample 112. In this connection, diffusable label 104, 104' is situated in the test chemistry layer 118 before wetting 108 of the test field 100. The compositions of the layers 118 are specified in Tables 1 and 2 below. The curves in FIGS. 2-9 were detected in reflectance. In this connection, detection in reflectance or detection of a reflectance value generally refers to an optical measurement based on reflection of waves, especially light or reflection of diffuse, undirected waves. Reflectance can be detected in various ways such as, for example, at least one signal of a detector that detects reflected light being acquired. As indicated in FIGS. 2-9 on the vertical axis, reflectance can be simply specified as signal I in arbitrary units (symbolized by "[−]"). Alternatively, it is possible for the reflectance to be specified in other units, for example in the form of a surface-based measure of the reflectance (i.e., a degree of reflectance). It also is possible to specify a ratio of reflected energy to incident energy in percent, a so-called albedo value.

In the experiments, the layers were excited at 660 nm with a measurement instrument (e.g., a Gen5Red measurement instrument) having a LED that emits light at a wavelength of 660 nm and detected in reflectance with a BPW34 silicon detector. For measuring behavior of the various dyes, use was made of test elements 50 having test fields 100 on a test support 60 as shown in FIGS. 1a-d. In some experiments, a further test chemistry layer 118, 120, which contained not only the detection reagents but also a varying percentage of dye (i.e., 0.05% or 0.1%) was applied to the reactive layer 118. The former is hereinafter called the label layer 120.

Two different layers, the composition of which is specified in Tables 2 and 3, were applied to a Pokalon film serving as test support 60 by doctor blading at a rate of about 5 m/min. The Pokalon film of the N332EM type from Lonza (Germany) is matt on one side, corona-treated and about 140 μm thick. In the recipes of the test chemistry layer 118 and the label layer 120, use was made of glucose dehydrogenase together with the coenzyme carba-NAD (cNAD). This was measured photometrically at 360 nm from the side opposite the sample input side with the BPW34 silicon detector. The diffusion of diffusable label 104, 104' was measured on the underside of the test field, (i.e., opposite the sample input side) with the aid of a light-emitting diode and a detector.

Dyes were selected, the absorption maximum of which is distinctly different with respect to the wavelength at which the glucose reaction is detected. In addition, the detection reagents were selected so as not exhibit any appreciable absorption. Furthermore criteria for the selected diffusable label were water-solubility and good chemical and light stability and availability.

Table 1 below specifies the diffusable labels (e.g., dyes) investigated, with their structural formulae and absorption maxima in various solvents.

TABLE 1

Name, structural formula and absorption maximum (in the media indicated within parentheses).

| Dye | Structure | Absorption |
| --- | --- | --- |
| Erioglaucine | 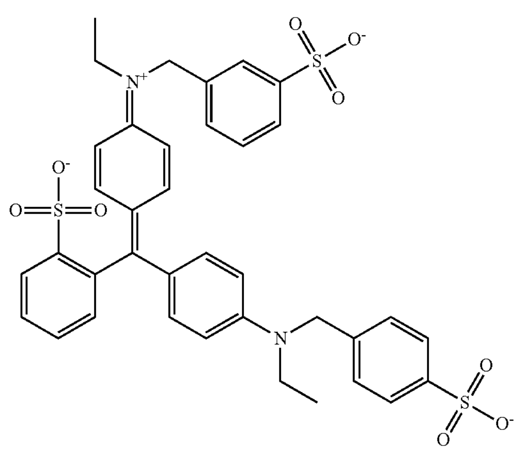 [SMILES: CCN(Cc1ccc(S(=O)(=O)[O-])cc1)c1ccc(C(=C2C=CC(=[N+](CC)Cc3cccc(S(=O)(=O)[O-])c3)C=C2)c2ccccc2S(=O)(=O)[O-])cc1] | 625 nm ($H_2O$) |
| Indigo carmine | 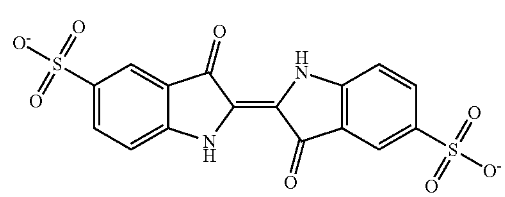 [SMILES: O=C1/C(=C2\Nc3ccc(S(=O)(=O)[O-])cc3C2=O)Nc2ccc(S(=O)(=O)[O-])cc21] | 608 nm ($H_2O$) |

TABLE 1-continued

Name, structural formula and absorption maximum (in the media indicated within parentheses).

| Dye | Structure | Absorption |
|---|---|---|
| Hydroxynaphthol blue | 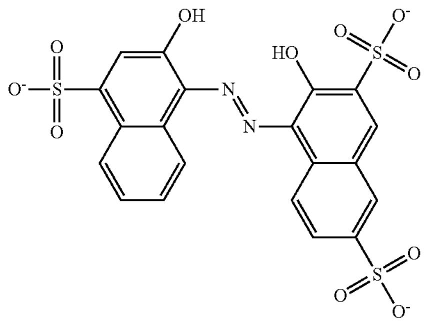 [SMILES: O=S(=O)([O-])c1ccc2c(/N=N/c3c(O)cc(S(=O)(=O)[O-])c4ccccc34)c(O)c(S(=O)(=O)[O-])cc2c1] | 650 nm (MeOH/H$_2$O) |
| 1,1-Diethyl-4,4-carbocyanine iodide (1260) | 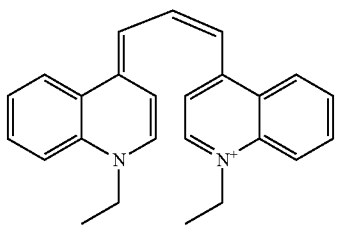 [SMILES: CCN1C=C/C(=C\C=C/c2cc[n+](CC)c3ccccc23)c2ccccc21] | 703 (648) nm (MeOH) |
| Amaranth | 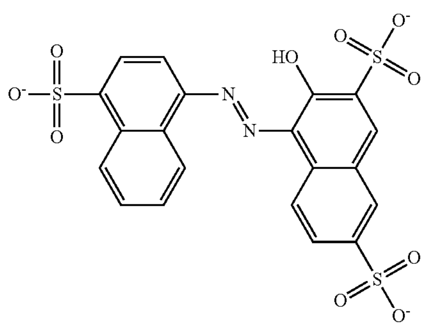 [SMILES: O=S(=O)([O-])c1ccc2c(/N=N/c3ccc(S(=O)(=O)[O-])c4ccccc34)c(O)c(S(=O)(=O)[O-])cc2c1] | 521 nm (H$_2$O) |

These dyes were added in different ratios as dry substance to the test fields 100 of the test elements 50 of FIGS. 2-9. The proportion of dye is indicated in the individual figure descriptions.

The makeup of the test chemistry layer 118 and label layer 120 for the subsequent experiments is specified in both Tables 2 and 3 below.

TABLE 2

1$^{st}$ test chemistry layer.

| S | Subst. (manufacturer) | Conc | W-Rec g/m$^2$ | Rec g/100 g | Actual g | MR | Sd g | spDa g/m$^2$ |
|---|---|---|---|---|---|---|---|---|
| 1 | Thickener | 7% | 19.961 | 14.84 | 103.93 | | | |
| | H$_2$O | | 15.606 | 11.61 | | 806.9 | 0.00 | |
| | Gantrez S97 (ISP Corp.; New Jersey) | | 1.397 | 1.04 | | 70.0 | 1.397 | 0.37 |
| | NaOH, 16% | pH = 6.8 | 2.958 | 2.20 | | 123.1 | 0.473 | 0.13 |
| | Suspension | | 33.598 | 24.99 | 175.10 | | | |
| 5 | Water, dd. | | 30.60.152 | 22.76 | | 182.20 | | 0.00 |
| 6 | Sipernat FK 320DS (Evonik) | | 3.00 | 2.23 | | 17.80 | 2.998 | 0.80 |
| | Wetting agent/other | | 12.88 | 9.58 | 67.12 | | | |
| 2 | Mega 8 | | 0.300 | 0.22 | 1.56 | | 0.300 | 0.08 |
| 3 | Geropon | | 0.040 | 0.03 | 0.210 | | 0.040 | 0.01 |
| 7 | Propiofan-70VAR (BASF) | | 8.044 | 5.98 | 41.90 | | 4.022 | 1.07 |

TABLE 2-continued

1st test chemistry layer.

| S | Subst. (manufacturer) | Conc | W-Rec g/m² | Rec g/100 g | Actual g | MR | Sd g | spDa g/m² |
|---|---|---|---|---|---|---|---|---|
| 4 | PVP 25000 (Fluka) | | 0.999 | 0.74 | 5.20 | | 0.999 | 0.27 |
| 8 | K—PO₄ buffer, pH 6.8 (Merck) | 1M | 3.50 | 2.60 | 18.25 | | 0.483 | 0.13 |
| 9 | Enzyme solution | | 68.03 | 50.59 | 354.50 | | | |
| | K—PO₄ buffer, pH 6.8 (Merck) | 0.1M | 31.0 | 23.05 | | 177.50 | 0.43 | 0.12 |
| | cNAD-Na (Roche) | | 5.98 | 4.45 | | 34.2 | 5.98 | 1.60 |
| | GlucDHmut2 #4 (kU/g)/(kU/m²) (Roche) | | 3.0/ 915.00 | 2.23/ 680.46 | | 17.2 | 3.00 | 0.80/ 244.14 |
| | Water, dd. | | 28.0 | 20.86 | | 160.6 | | 0.24 |
| | pH before adjustment | 6.8 | | | | | | |
| | pH after adjustment | 6.77 | | | | | | |
| | NaOH, 16% for fine adjustment | | | | | | 0.000 | |
| | Total | | 134.47 | 100.00 | 700.65 | | 41.09 | 18.96 |

S: sequence;
Subst: substance;
MR: master ratio;
Conc: concentration;
W-Rec: working recipe;
Rec: recipe;
Sd: solid;
spDa: specific dry application The substances were applied to the Pokalon film of a test field of a test support in the sequence specified. Subsequently, the layers were dried at about 50° C. for about 15 min.

TABLE 3

2nd test chemistry layer

| S | Subst. | Conc | W-Rec g/m² | Rec g/100 g | Actual g | PS | Sd g | spDa g/m² |
|---|---|---|---|---|---|---|---|---|
| | Sy | | 69.503 | 71.66 | 537.37 | | | |
| 2 | K—PO₄, pH = 6.8 | 1M | 8.800 | 9.07 | 68.04 | | 1.25 | 0.58 |
| 3 | ZrO₂ (FCM) | | 35.551 | 36.65 | 274.88 | | 35.55 | 16.40 |
| 1 | Water, dd. | | 25.152 | 25.93 | 194.45 | | | |
| | Thickener | 7% | 23.329 | 24.05 | 180.35 | | | |
| 4 | H₂O | | 18.824 | 19.41 | | 806.9 | 0.00 | 0.00 |
| | Gantrez S97 | | 1.633 | 1.68 | | 70.0 | 1.63 | 0.75 |
| | NaOH, 16% | pH = 6.8 | 2.872 | 2.96 | | 123.1 | 0.46 | 0.21 |
| | Wetting agent/other | | 4.165 | 4.29 | 32.17 | | | |
| 5 | Mega 8 | | 0.235 | 0.24 | 1.82 | | 0.24 | 0.11 |
| 6 | Propiofan | | 3.930 | 4.05 | 30.35 | | 1.97 | 0.91 |
| 7 | NaOH, 16% | | | | | | 0.00 | 0.00 |
| | pH before adjustment: | 6.7 | | | | | | |
| | Total | | 96.997 | 100.00 | 749.89 | | 41.09 | 18.96 |

S: sequence;
Subst: substance;
Sy: slurry;
Conc: concentration;
W-Rec: working recipe;
Rec: recipe;
PS: partial solutions;
Sd: solid;
spDa: specific dry application The substances were applied to the 1$^{st}$ layer on the test field of the above test support in the sequence specified. The application took place by means of a doctor-knife blade, which evenly applies the aforementioned chemicals to the test support by means of doctor blading over table. The particular dye was applied to the test support as the last step. The coating took place at room temperature and a relative air humidity of about 43%. Subsequently, the layer was dried at about 50° C. for about 20 min.

The buffer solutions used were prepared according to Table 4.

TABLE 4

Buffer solutions.

| | g | |
|---|---|---|
| Gantrez solution, 7%, pH = 6.9 | | |
| Water, dd. | 806.9 | |
| Gantrez S97 533448 | 70.0 | 7.0% |
| NaOH, 16% | 123.1 | |
| | 1000.00 | |
| | | 6.92 |
| pH (6.8 +/− 0.1): | | |
| Silicic acid suspension (water, dd.) | | |
| Silicic acid, Sipernat FK320DS 533235 | 17.8 | 8.9% |
| Water, dd. | 182.2 | |
| | 200 | |
| K$_2$HPO$_4$ solution, 1M (fill up to 500 mL up to calibration mark) | | 174.18 g/mol |
| K$_2$HPO$_4$ (03593622001/# 51833200) | 87.10 | 15.4% |
| Water, dd. | 478.60 | |
| | 565.70 | |
| KH$_2$PO$_4$ solution, 1M (fill up to 500 mL up to calibration mark) | | 136.09 g/mol |
| KH$_2$PO$_4$ | 68.05 | 12.5% |
| Water, dd. | 476.76 | |
| | 544.81 | |
| K phosphate buffer, pH = 6.8, 1M | | 13.8% |
| Initially charged K$_2$HPO$_4$ solution (15.4%) | 400.00 | |
| KH$_2$PO$_4$ solution (12.5%) | 494.80 | |
| Total buffer at pH 7.0 | 894.80 | |
| pH (6.8 ± 0.1): | | 6.8 |
| K phosphate buffer, 0.1M, pH = 6.8 (fill up to 1 L up to calibration mark) | | |
| K phosphate buffer, 1M, pH = 6.8 | 100 | |
| Water, dd. | 900 | 1.40% |
| | 1000 | |
| pH (6.8 ± 0.1): | | 6.8 |

Test elements having the dyes from Table 5 were prepared in a manner as explained above and tested in experiments.

TABLE 5

Composition of the test fields in the various experiments (as described and shown in FIGS. 2-9).

| | 1st layer (66 μm), final pH 6.75 | 2nd layer (58 μm) |
|---|---|---|
| V1 | Standard | Standard |
| V2 | Standard + 0.05% by weight of amaranth (17.9 mg/m$^2$) | Standard |
| V3 | Standard + 0.1% by weight of amaranth (35.8 mg/m$^2$) | Standard |
| V4 | Standard + 0.05% by weight of erioglaucine (17.9 mg/m$^2$) | Standard |
| V5 | Standard + 0.1% by weight of erioglaucine (35.8 mg/m$^2$) | Standard |
| V6 | Standard + 0.05% by weight of hydroxynaphthol blue (17.9 mg/m$^2$) | Standard |
| V7 | Standard + 0.1% by weight of hydroxynaphthol blue (35.8 mg/m$^2$) | Standard |
| V8 | Standard + 0.05% by weight of indigo carmine (17.9 mg/m$^2$) | Standard |
| V9 | Standard + 0.1% by weight of indigo carmine (35.8 mg/m$^2$) | Standard |
| V10 | Standard + 0.05% by weight of 1,1-diethyl-4,4-carbocyanine iodide (1260) (17.9 mg/m$^2$) | Standard |
| V11 | Standard + 0.1% by weight of 1,1-diethyl-4,4-carbocyanine iodide (1260) (35.8 mg/m$^2$) | Standard |

The dye was added as a dry substance to the 1$^{st}$ layer before application to the test field and homogenized with a paddle stirrer (about 200 rpm), which was subsequently sieved and centrifuged.

All the dyes exhibited a temperature-dependent diffusion (e.g., an "outward flow") into the upper blood, which was reflected in an increase in the reflectance signal as the concentration of the absorbing dye in the label layer 120 was reduced. The respective magnitude of the dependence depended on the structure of the particular dye.

The example described herein concerns kinetics of erioglaucine, which exhibited the strongest temperature dependence and were not dependent upon glucose concentration.

Figure 2:
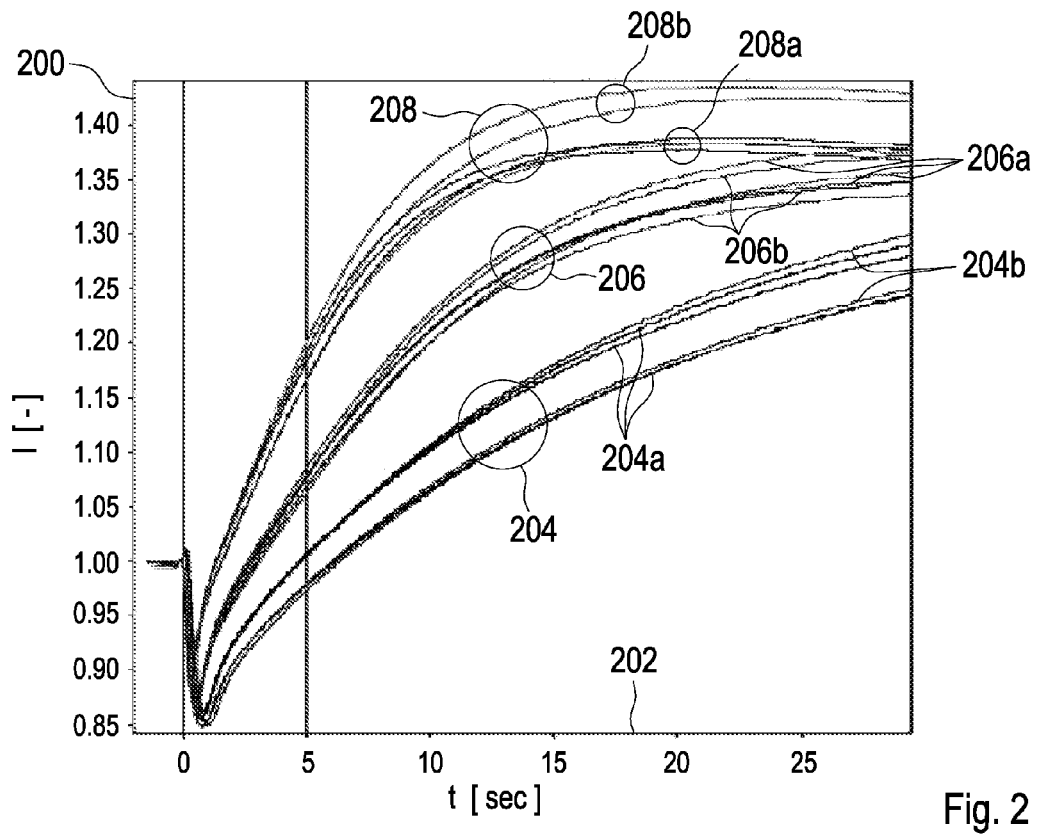
FIG. 2 shows curve profiles after wetting of a test field including 0.05% erioglaucine at different temperatures with samples of varying glucose content.

FIG. 2 shows various curve profiles of diffusion kinetics of erioglaucine within the test field before and after wetting of the test field with sample (in this case, blood) on the basis of three different families of curves 204, 206 and 208 with the intensity of the reflected light being measured. Light of wavelength 625 nm was irradiated onto the test field. The test field includes 0.05% erioglaucine as label in the first region 114 of the test field 100 shown in FIG. 1b. Light of wavelength 625 nm was guided by the underside of the test field 100 directly onto the label layer 120, and the detector recorded reflected light from this test field side.

Various test fields were subjected to a temperature-dependent measurement, by blood having two glucose concentrations applied to the layer and being measured at 660 nm. In the curve profile, it is possible to distinguish three different families of curves, where the first family of curves 204 exhibits a reflection of the test field at 5° C. and two different glucose concentrations (e.g., 0 mg/dl 204a and 550 mg/dl 204b) in the sample. The second family of curves 206 was measured at 25° C. either with 0 mg/dl glucose supplement 206a or 550 mg/dl glucose supplement 206b, whereas the third family of curves 208 was measured at 45° C. One part of the curves was generated with a sample without addition of glucose 208a, whereas a second part was ascertained with an addition of 550 mg/dl glucose 208b.

As shown in FIG. 2, the slope of the kinetics is strongly dependent on the temperature—at 5° C., the outward flow of the dye is distinctly slower than in the case of 25° C., and the rate is in turn slower than at 45° C. With the concentration of the dye in the label layer, it is possible to influence the level and the speed of the end signal. The quantity of analyte (i.e., glucose) had no influence on the diffusion of the label and vice versa, as can be seen from the curve profiles.

Figure 3:
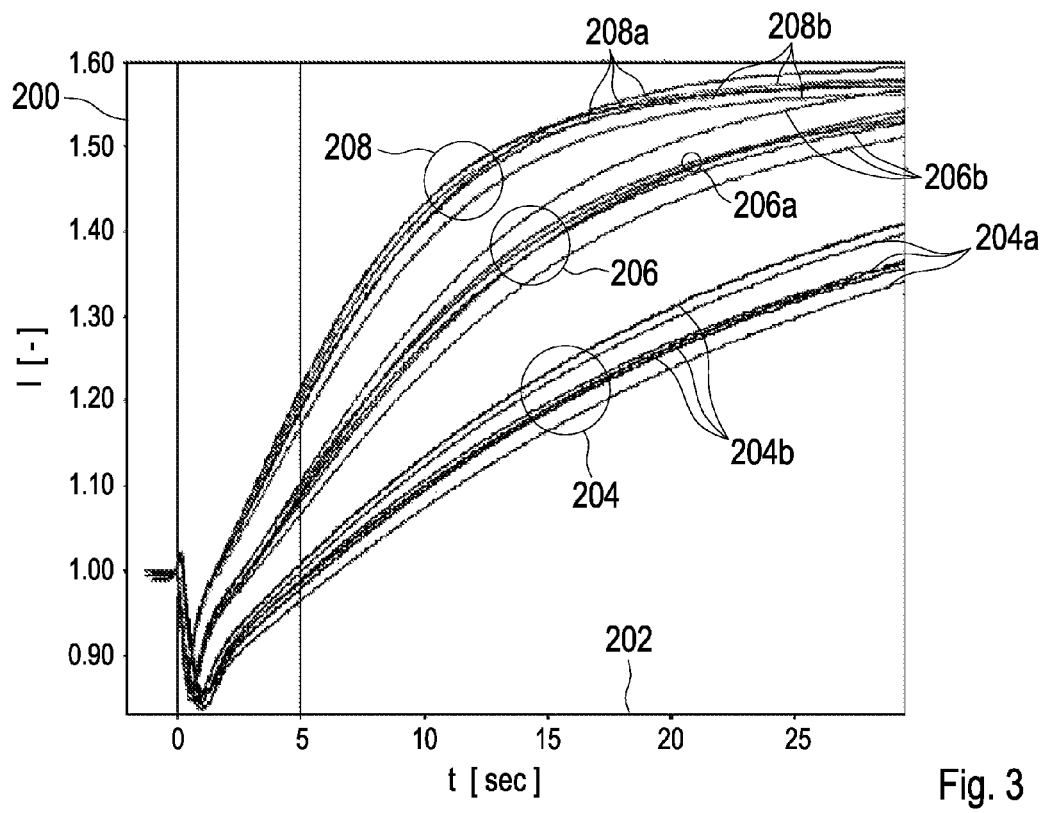
FIG. 3 shows curve profiles after wetting of a test field including 0.1% erioglaucine at different temperatures.

As shown in FIG. 3, similar results were achieved with a concentration of 0.1% erioglaucine in the label layer 120 in the test field 100. Here too, it was possible to distinguish three families of curves 204, 206 and 208, which were determined for the temperatures 5° C., 25° C. and 45° C. for the first family of curves 204, the second family of curves 206 and the third family of curves 208, respectively.

In both FIGS. 2 and 3, it is not possible to distinguish the different glucose concentrations from one another at the respective temperatures, and this is shown by the subgroups 204a, 206a and 208a for 0 mg/dl glucose and the subgroups 204b, 206b and 208b having in each case 550 mg/dl glucose. From these curve profiles, it can be deduced that, although the diffusion of erioglaucine is temperature-dependent, it is not dependent on the analyte concentration. For this reason, this dye is suitable for inferring the temperature of the sample on the basis of its diffusion rate.

Figure 4:
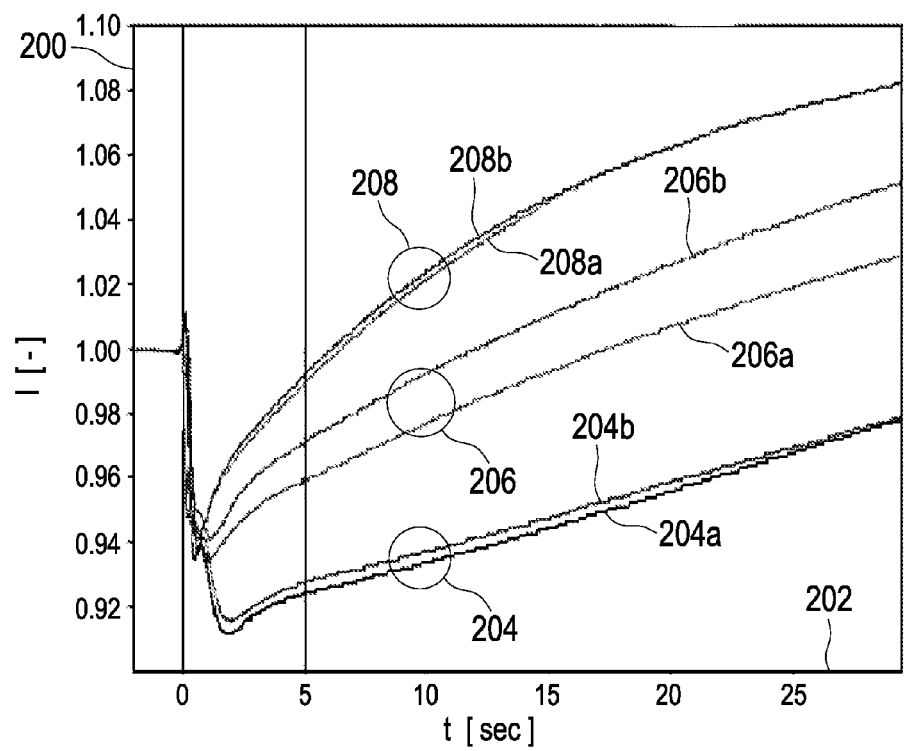
FIG. 4 shows curve profiles after wetting of a test field including hydroxynaphthol blue at different temperatures.

As shown in FIG. 4, it was possible to demonstrate the inventive concept not only for erioglaucine but also for hydroxynaphthol blue. Here too, the dependence of the diffusion rate of the label was measured at different temperatures—5° C. for the family of curves 204, 25° C. for the family of curves 206 and 45° C. for the third family of curves 208, at different glucose supplements. The basic finding was that, while the diffusion rate of hydroxynaphthol blue is temperature-dependent but not dependent on the analyte concentration.

Figure 5:
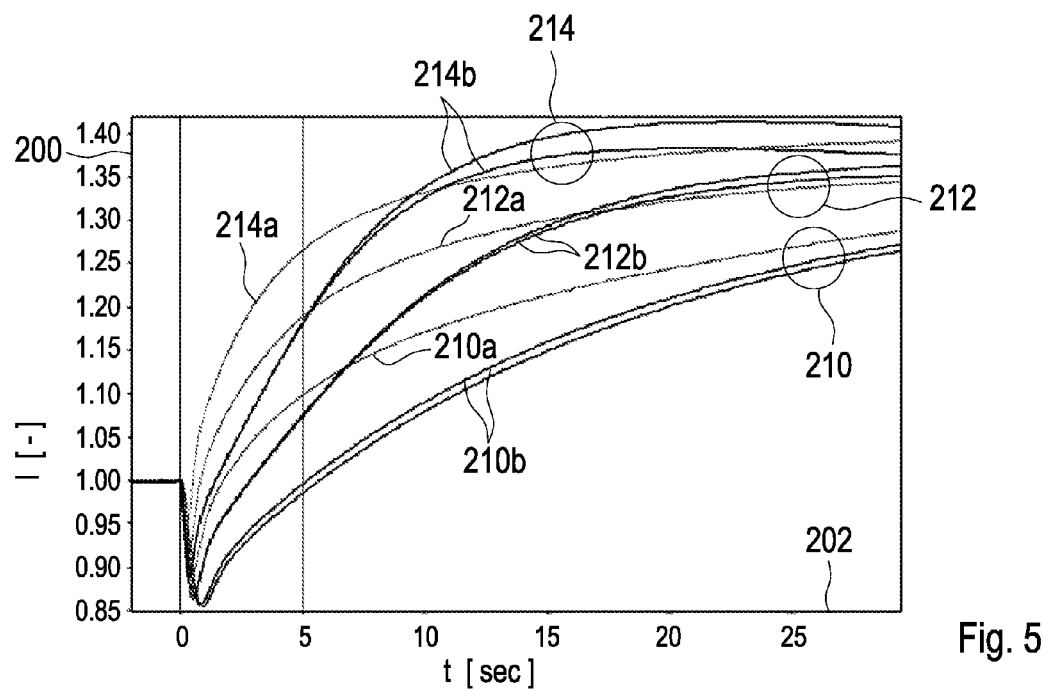
FIG. 5 shows curve profiles after wetting of a test field including 0.05% erioglaucine with blood or water at different temperatures.

As shown in FIG. 5, it was possible to additionally show that the diffusion rate of erioglaucine was dependent not only on the temperature but also on Hct of the sample. To this end, reflection curves were recorded at different temperatures—5° C. for the family of curves 210, 25° C. for the family of curves 212 and 45° C. for the family of curves 214. In this connection, which profile the curve takes depends on Hct of the sample. For instance, curves can be distinguished at 5° C. in terms of their kinetics, depending on whether they have blood as sample, as shown for the family of curves 210b, or whether, as for the family of curves 210a, the sample consists of water. Likewise, the family of curves 212 can be distinguished in terms of its profile, on the basis of curves for blood samples 212b at 25° C. and curves for water samples 212a at 25° C. The other family of curves 214 at 45° C. can be distinguished according to the samples of water having the curve 214a and blood having the curves 214b. As can be seen, the label diffuses more rapidly out of the test field 100 at elevated temperature. In addition, a varying diffusion rate at the respective temperatures can be distinguished for varying Hct. For example, at the same temperature of 5° C., a distinctly higher diffusion was found at lower Hct. On the basis of these curve profiles, it is consequently possible to infer together the influence of temperature and Hct. If the temperature is known, it is possible, on the basis of the diffusion of diffusable label, to infer the Hct, and vice versa.

To further investigate the influence on the measurements by Hct, the test chemistry layer 118 containing diffusable label 104, 104' in the form of erioglaucine was investigated, particularly the outward flow of erioglaucine from the layer.

Figure 6:
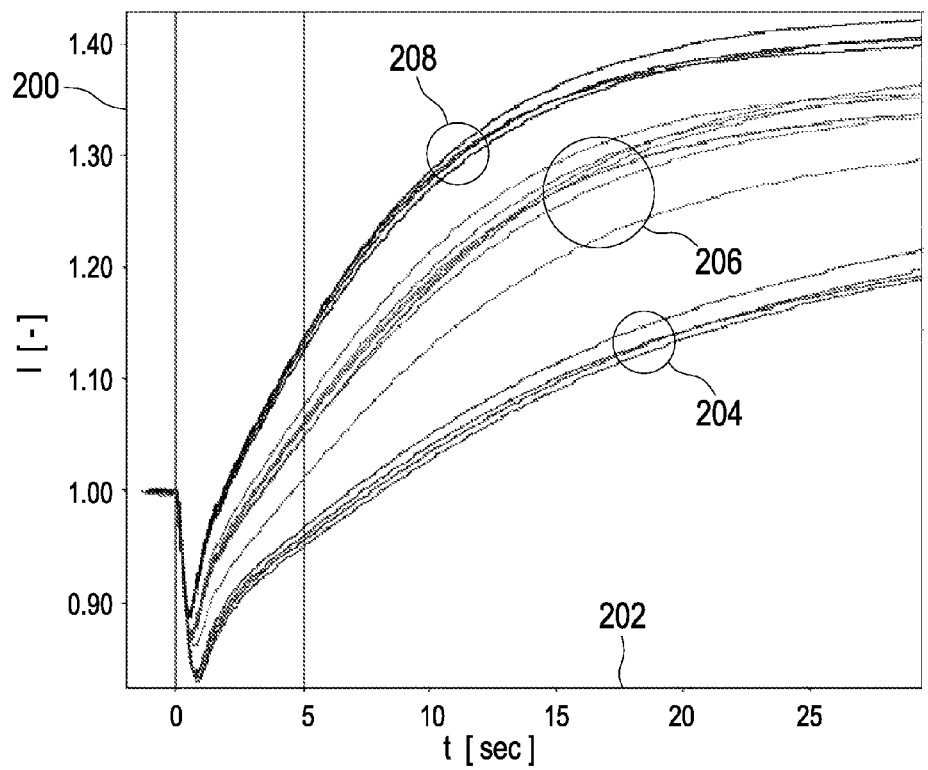
FIG. 6 shows curve profiles after wetting of a test field including 0.05% erioglaucine with blood containing varying Hct.

FIG. 6 shows curve profiles of three different samples having varying Hct, the test field 100 being coated with 0.05% erioglaucine. The curves of the family of curves 204 have a Hct of 65%, whereas the curves of the family of curves 206 have a Hct of 45%, and the curves of the family of curves 208 a Hct of 25%. In this connection, the applied sample did not contain any glucose. Here, the samples are blood samples brought to 0 mg/dl glucose by rolling at room temperature, sample movement was generated by the rolling and practically complete degradation of any glucose present taking place overnight owing to the cells contained in the sample.

Figure 7:
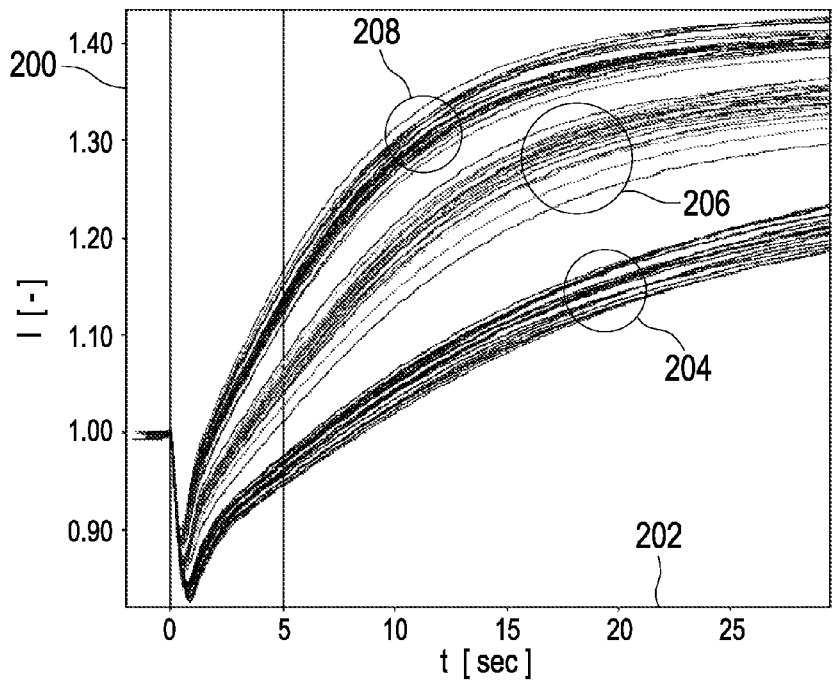
FIG. 7 shows curve profiles of measurements on different test fields including 0.05% erioglaucine with samples having varying Hct at varying glucose concentrations.

FIG. 7 shows families of curves 204, 206 and 208 having respectively 65%, 45% and 25% Hct in blood were recorded, samples having different glucose concentrations being found in the families of curves. For each family of curves 204, 206 and 208, glucose concentrations of 0, 90, 150, 350 and 550 mg/dl were recorded. On the basis of these families of curves, it likewise can be seen that diffusion of the diffusable label was approximately independent of the concentration of analyte 117 in the sample, but that there was a dependence of the kinetics on Hct. Consequently, Hct of the sample can be determined from the curve profile.

Alternatively, it is also possible at a particular time, as indicated here after 5 seconds, to ascertain the reflection difference in relation to time 0, corresponding to the time of sample input, and to ascertain therefrom the Hct of the sample.

Figure 8:
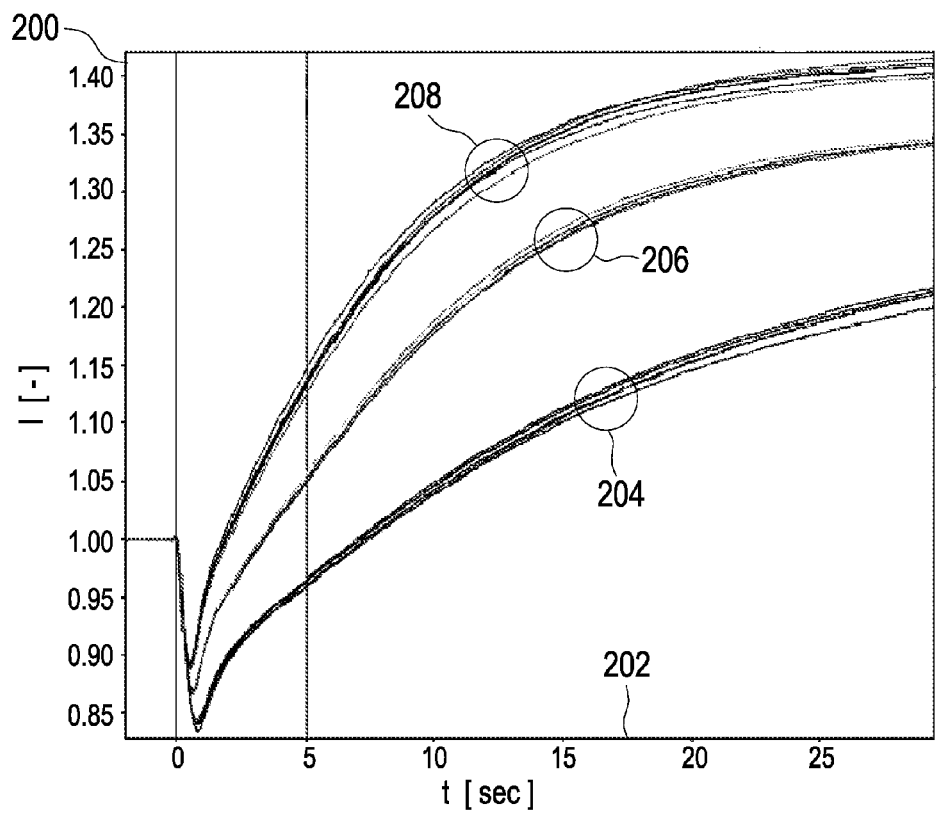
FIG. 8 shows curve profiles of test fields including erioglaucine with samples having varying Hct at varying glucose concentrations.

FIG. 8 shows the mean values for the respective glucose concentrations of 0, 90, 150, 350 and 550 mg/dl from the families of curves 204, 206 and 208 from FIG. 7. This clarifies the independence of the curve profiles from the glucose concentration of the sample.

Figure 9:
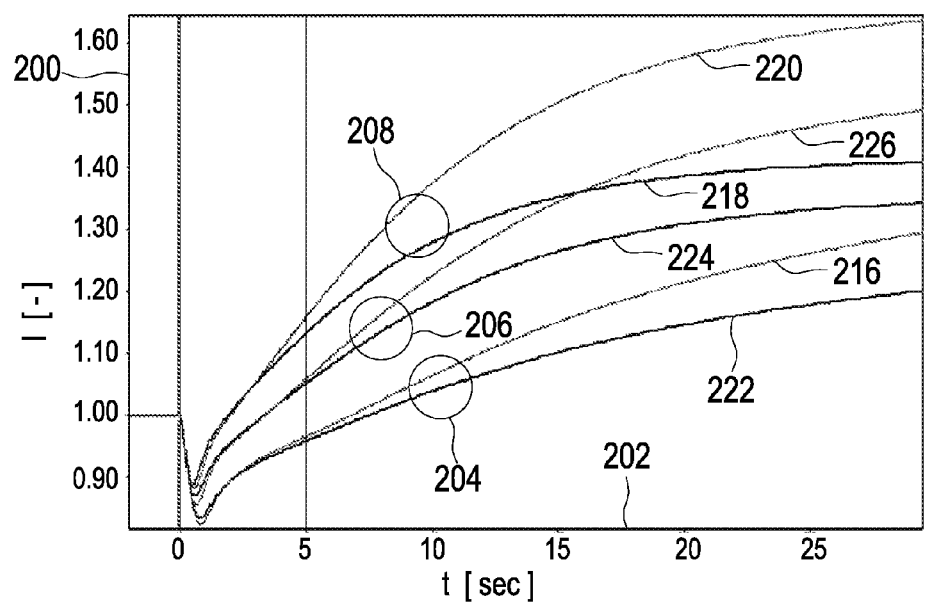
FIG. 9 shows curve profiles of test fields including 0.05% or 0.1% erioglaucine.

FIG. 9 shows three families of curves 204, 206 and 208, and within the family of curves 204, a curve 216 for a test field was doped with 0.05% erioglaucine, whereas the curve 222 originates from a test field containing 0.1% erioglaucine. Both curves were recorded with an aqueous solution and a Hct of 65%. The family of curves 206 was recorded with a Hct of 45%, and the family of curves 208 with a Hct of 25%. Also in the case of the family of curves 206, a curve 224 having 0.05% erioglaucine can be distinguished from a curve 226 having 0.1% erioglaucine, whereas in the family of curves 208, a curve 218 having 0.05% erioglaucine and a curve 220 having 0.1% erioglaucine can be distinguished. Generally, the measurements were stopped after 4 to 5 seconds to realize as short a measurement time as possible.

From the families of curves 204, 206 and 208, which each include two different diffusable label concentrations, it can be seen in the case of the line drawn at 5 seconds after sample input that a distinction between the two concentrations of 0.1 and 0.05% of erioglaucine can barely be distinguished. This means that even in the event of a decrease in diffusable label in a test element over the service life, any restriction of the correction means need not be feared.

Altogether, it can be observed that all the dyes investigated in FIGS. 2-9 exhibited a temperature-dependent outward flow into the supernatant from blood after wetting of the test field. This becomes apparent in an increase in the reflectance signal, since the concentration of the absorbing dye is lowered in the test layer. The particular magnitude or the particular extent of the dependence on the temperature depends on the structure of the particular dye.

Figure 10:
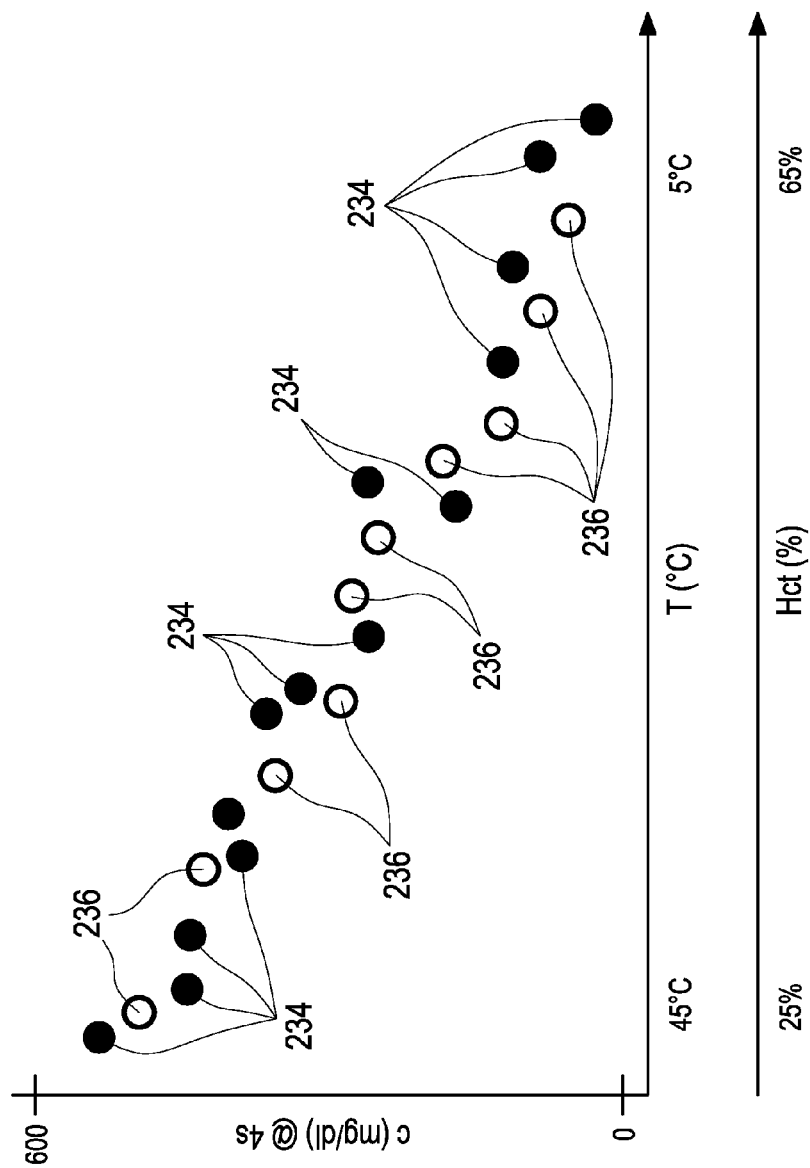
FIG. 10 shows a diagram of the influence of temperature and Hct on an analyte measurement signal after 4 seconds.

FIG. 10 shows the behavior of an analyte signal of a sample, in this case glucose in blood, at different temperatures and different Hct. Here, the analyte signal is plotted in FIG. 10 on the vertical axis and identified by c and specified in mg/dl. As used herein, "analyte signal" means any desired measurement value or any desired measurement variable or variable derived from a measurement that reflects the analyte concentration or that correlates with the analyte concentration or that makes it possible to infer the analyte concentration. The analyte signal can, as an alternative to the specification in mg/dl, also be specified in other units such as, for example, in units of a detector signal in reflectance values or similar units. In FIG. 10, the analyte signal was acquired at a time of 4 seconds after wetting of the test field with the sample, and this is symbolized as "@ 4 s". As noted above, the values of the analyte signal shown in FIG. 10 are not measurement values, but rather schematic, fictitious values reflecting a typical profile of the analyte signal.

FIG. 10 also shows, diagrammatically, dependencies of the analyte signal on two different influences of varying properties of the sample—the temperature T, specified in ° C., and a Hct value, specified in percent. These properties are shown on the horizontal axis. In this connection, fictitious analyte values which, for example, could be acquired as part of a series of measurements with variation of the temperature T shown as filled-in circles and identified by the reference number 234. Analyte values that could be acquired as part of a series of measurements with variation of the Hct are shown as open circles and identified by the reference number 236.

The values shown in FIG. 10 could, for example, be acquired with a measurement assembly in which the sample is applied from an application side to a test field containing the test chemistry and optionally the label. The test field is irradiated with an analyte detector light source by means of a first LED from a detection side of the test field that is opposite the application side, and light scattered on the test field acquired by means of a photosensitive detector such as, for example, a photodiode, to obtain a reflectance value. The reflectance value of the analyte measurement can then be converted by means of a known, fixed rule into the analyte concentration (uncorrected), specified in mg/dl or in other concentration units. The analyte detector light source can be adapted in terms of its spectral properties in such a way that it has a wavelength that is absorbed by a dye of the test chemistry. For example, the analyte detector light source can emit at a wavelength of 360 nm.

The profile of the points for variation of the temperature 234 shows a lowering of the measurement values for the analyte glucose with sinking temperature. This means that the user of a conventional test element without temperature correction receives a higher analyte measurement value when the temperature is higher than during the calibration and a lower value when the temperature during the measurement is lower than that during the calibration of the system. It is likely that this behavior is caused by a lowering of the temperature generally inhibiting in particular diffusion behavior, and so the analyte to be detected advances more slowly toward the test chemistry than at a higher temperature. In addition, the actual detection reaction for detecting the analyte may be slowed down.

An inverse behavior was exhibited by the measurement signal with regard to Hct in the sample. As shown in FIG. 10, on the basis of the measurement points for Hct 236, that the measurement signal for glucose decreases when the Hct increases. The measurement signal for glucose decreased within the temperature range of 5° C. to 45° C. to the same extent as in the case of a rise in Hct from 25% to 65%. It is likely that the cause of this behavior is likewise to be found in an inhibition of diffusion processes by the increased Hct.

Both aforementioned effects are generally not directly separable, but this is irrelevant for a correction. For example, it is generally possible to achieve a correction for a combination of a particular Hct at a particular temperature without Hct and temperature being known. Alternatively, it would, however, also be possible to independently determine one of these interfering variables, such as temperature and Hct (i.e., independently of the diffusion of label). For example, it would be possible to use at least one temperature sensor that can determine an ambient temperature and/or a temperature of the test element and/or a temperature of the sample (generally in the context of the present disclosure, no distinction is generally made between these temperatures). With knowledge of the temperature, it is then possible to achieve a correction by means of the ascertained label diffusion for a particular Hct.

As will be explained in more detail below, the correction of the analyte concentration can be carried out so that an analyte concentration at, for example, 21° C. or 25° C. (room temperature) and a Hct of 40% is ascertained as corrected values of the analyte concentration, and so corrected analyte concentrations acquired under different conditions (temperature, Hct) can be compared with one another.

Figure 11:
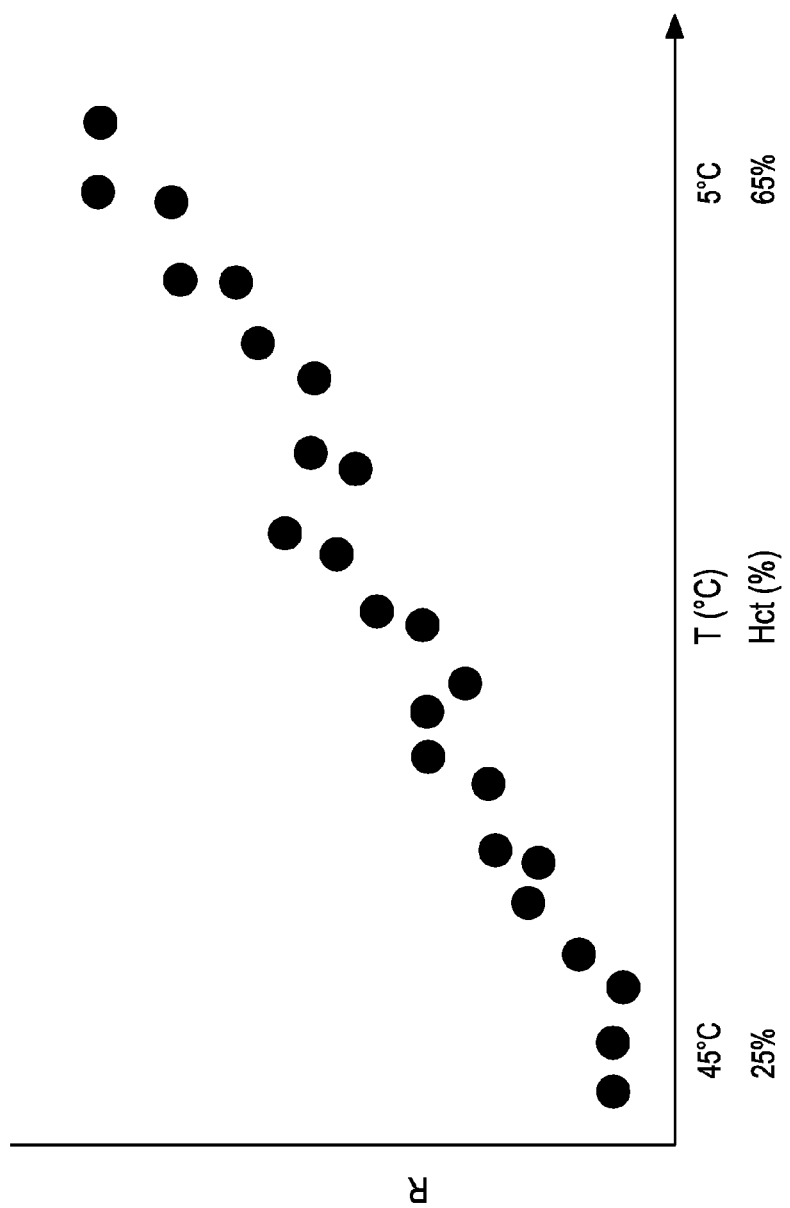
FIG. 11 shows a diagram of the influence of temperature and Hct on the reflectance behavior of a diffusable label.

By contrast, FIG. 11 shows the influence of the temperature and/or Hct on a diffusable label signal. Again, fictitious values were plotted, which show symbolically a typical profile of a label signal. It would be possible to acquire the values of the label signal with a measurement assembly analogous to the measurement assembly described above in relation to FIG. 10 or with the same measurement assembly. For example, it would be possible to apply the sample from an application side to a field containing the label and optionally also the test chemistry, a label field and/or a test field. The test field can be irradiated with a label detector light source by means of a second LED from a detection side of the test field that is opposite the application side, and by means of a photosensitive detector such as, for example, a photodiode. Light scattered on the label field and/or test field can be acquired to obtain a reflectance value R. In this connection, the label detector light source can be adapted in terms of its spectral properties so that it has a wavelength that is absorbed by a label. For example, the label detector light source can emit at a wavelength of about 660 nm.

FIG. 11 shows the reflectance behavior R (specified on the vertical axis without units) of erioglaucine, which exhibits the same behavior in the case of temperature change as in the case of Hct change within a particular range of this parameter. In this connection, the reflectance R can be acquired on a label field as a function of time after wetting of the label field or test field with the sample. After 4 sec, the measurement can be stopped, and the reflectance value R recorded at this time.

FIG. 11 also shows that the reflectance of the label increases upon lowering of the temperature from 45° C. to 5° C., as strongly as the increasing of Hct from 25% to 65%. Again, it is thus possible to record two effects that can be attributed to the two interfering variables, temperature and Hct. In the case of increasing temperature and decreasing Hct, the diffusion of the label into the sample is favored, and so the staining of the label field and/or of the test field containing the label, as viewed from the detection side, decreases, resulting in the reflectance increasing. Conversely, in the case of decreasing temperature and increasing Hct, the diffusion of the label into the sample is inhibited, and so the staining of the label field and/or of the test field containing the label is preserved and the reflectance thus remains low. For example, the reflectance can again be acquired at a time of 4 s after application of the sample or at another predefined time after application of the sample. Again, both effects are typically separable only with difficulty. However, since the reflectance during the measurement of label is dependent on both interfering variables, the reflectance during the measurement of label, which is at least approximately independent of the analyte concentration, can allow jointly a total correction for both interfering variables.

Figure 12:
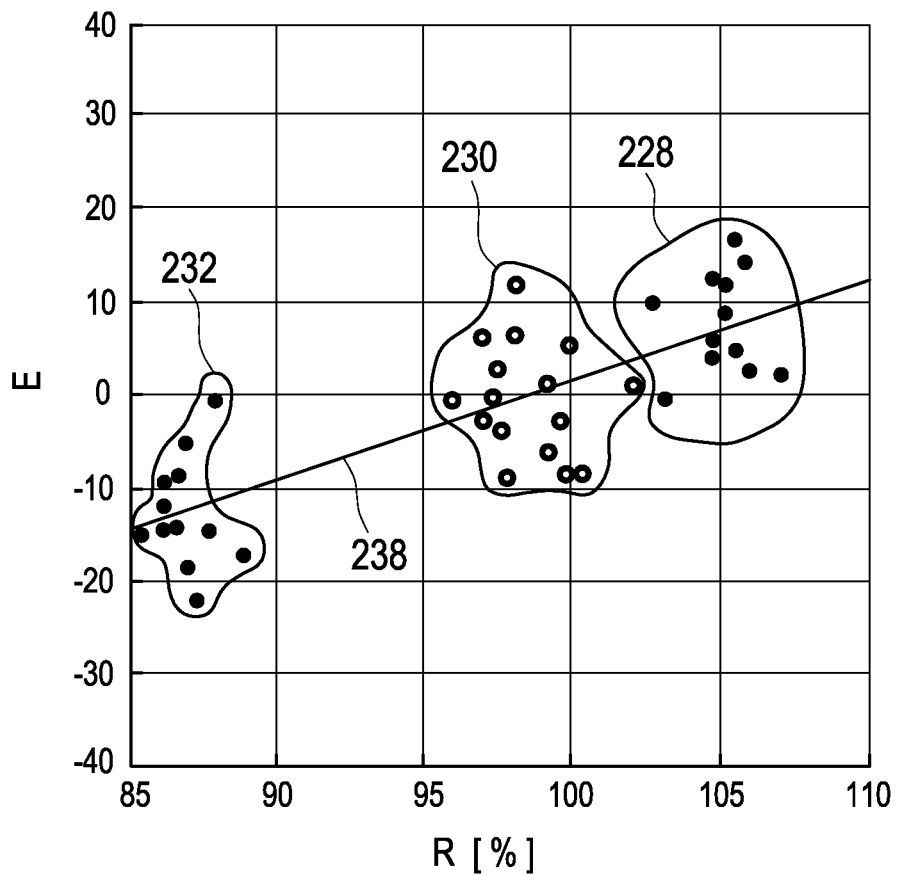
FIG. 12 shows a correlation between a system error during a glucose measurement and a reflectance measurement on a diffusable label field at varying Hct.
Figure 13:
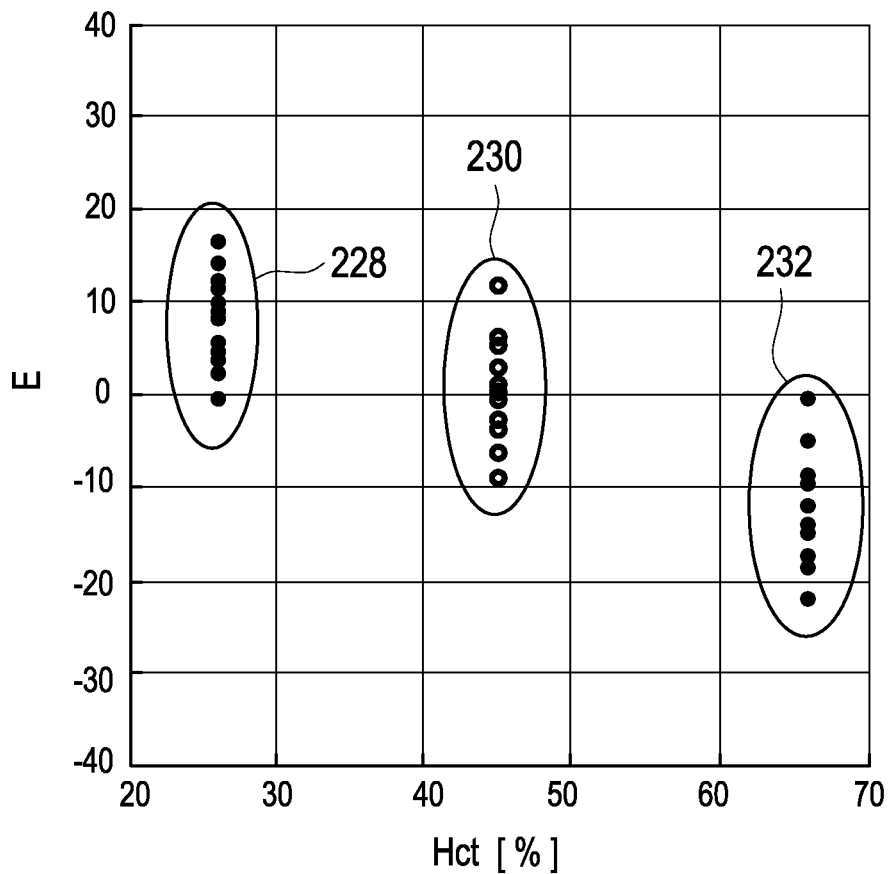
FIG. 13 shows a graph of system error of a conventional test element system at varying Hct without using a piece of correction information from the diffusable label.
Figure 14:
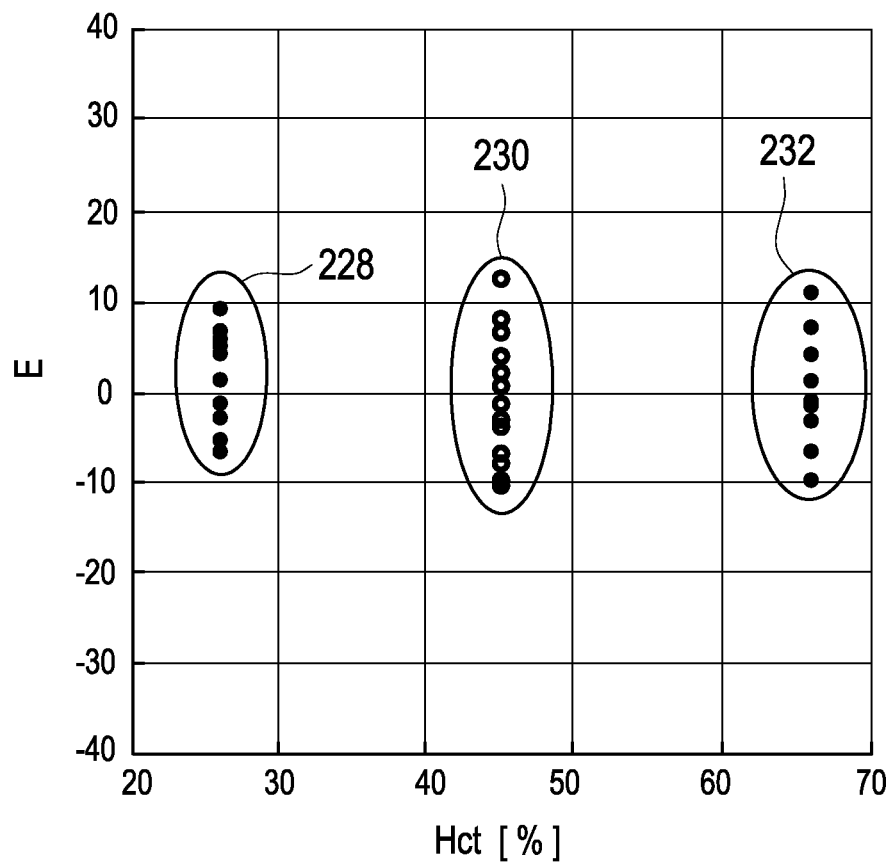
FIG. 14 shows a graph of system error of an exemplary test element system at varying Hct using a piece of correction information from the diffusable label.

FIGS. 12 to 14 show an alternative method of correcting a glucose measurement by a reflectance measurement of a label field. For these measurements, 10 to 50 samples having different glucose concentrations between 30 mg/dl and 550 mg/dl were measured optically, with reflectance measurements being carried out and subsequently the reflectance values being converted into corresponding glucose concentrations in a conventional manner (i.e., in a manner known to one of skill in the art without taking into account the Hct and the temperature). In this connection, 10-15 measurements were carried out in each case on samples having a predefined Hct, with measurements being carried out on samples having three different Hct values—in each case 10-15 measurements on samples having 25% (identified in FIGS. 12 to 14 by reference number 228), 10-15 measurements on samples having 45% (identified in FIGS. 12 to 14 by reference number 230), and 10-15 measurements on samples having 65% (identified in FIGS. 12 to 14 by reference number 232).

Plotted on the vertical axis in FIGS. 12 to 14 is "system error," which is identified by "E". In glucose measurement instruments, the system error is a variable known to one of skill in the art. The system error is specified in absolute units in the case of glucose concentrations up to 100 mg/dl, and in percent in the case of glucose concentrations above 100 mg/dl. The system error is calculated in each case from the measured value and the actual value of the glucose concentration, which, as explained above, is influenced by the diffusion of the glucose in the sample.

The actual value of the glucose concentration can be determined by means of a known laboratory method and/or by a known starting weight of glucose in a sample during preparation of the sample. To calculate the system error E, the deviation of the measured value from the actual value is determined by means of optical reflectance measurement on a test field. In the case of measured concentrations of up to 100 mg/dl, the absolute deviation is specified as system error. In the case of measured concentrations above 100 mg/dl, the deviation with respect to the actual concentration is expressed as a ratio.

FIG. 12 shows the reflectance R of a label field specified on the horizontal axis, which reflectance is influenced by the diffusion of the diffusable label in the sample. The diffusable label was erioglaucine, and reflectance was acquired 4 s after application of the sample to the label field or test field, analogously to the measurements in FIG. 11. Reflectance is specified here in percent, based on an absolute reflectance. Alternatively, it would be possible to plot other representations of results of a measurement of label on this horizontal axis.

FIG. 12 thus shows that the family of points exhibit a correlation between the system error E of the glucose measurement and the reflectance behavior of the label, which can be utilized for correction. The correlation can be described by a line, more particularly a standard curve, having the linear equation E=m·R+b, where the parameters m (slope) and b (axis intercept) can be determined from an alignment to experimental values, according to established methods. For example, this can be achieved by a so-called fit. By means of the parameters determined in this manner, it is subsequently possible to correct analyte measurements by firstly determining uncorrected values of a reflectance and/or an analyte concentration in the case of an analyte measurement, which values are then corrected by means of a correction factor corresponding to the known parameters of the correlation. Thus, a correction of the analyte measurement to a corrected reflectance and/or a corrected analyte concentration at 25° C. and 40% Hct can take place.

The correlation in FIG. 12 thus shows that the influence on the glucose measurement by Hct correlates with the influence on the label reflectance by the Hct. Exemplarily, a linear correlation was adopted for the correction of this influence, though more complex correlations also are possible. To quantify this correlation, a fitted line 238 was aligned to the measurement values in FIG. 12. The fitted parameters of said fitted line 238 the can be utilized to correct, after acquiring the reflectance of the label field, corresponding measurement values of the glucose concentration. This is shown in FIGS. 13 and 14.

FIG. 13 shows system error E for various Hct values in blood without use of the abovementioned piece of correction information as a function of Hct. It can be seen that, owing to the uncorrected measurement points, the system error scatters from about −22% in the case of a Hct of 65% right up to almost 20% in the case of a Hct of 25%.

By contrast, if these measurement values are corrected with the aid of the piece of correction information from the fitted lines 238, the scattering of the system errors can be drastically reduced. As shown in FIG. 14, the same measurement values were taken as basis, which were also taken as a basis of the measurement in FIG. 13. However, the measurement values were firstly corrected with the piece of correction information from the fitted lines 238 and subsequently the system error E was ascertained.

The system error can, for example, be described with the aid of a linear equation:

$$E = m^*R + b \qquad (1),$$

where E is the system error, m the slope of the lines, R the reflectance value and b the y-axis intercept of the lines.

With the aid of the error ascertained in this manner, it is possible to convert a later-ascertained, uncorrected glucose measurement value into a corrected glucose measurement value. The following arises:

$$gc_{corr} = gc_{uncorr} - E = gc_{uncorr} - m^*R - b \qquad (2),$$

where $gc_{corr}$=corrected glucose measurement value; $gc_{uncorr}$=uncorrected glucose measurement value; E=system error, m=slope of the lines, R=reflectance value; b=y-axis intercept.

The corrected results in FIG. 14 show that an efficient adjustment of the influence of the interfering variables temperature and Hct can be achieved by means measuring diffusable label and the correlation known owing to the measurement in FIG. 12. For instance, following the correction in FIG. 14, all families of points 228, 230 and 232, having respectively 25%, 45% and 65% Hct, are approximately within a band of about ±10% or ±10 mg/dl system error. This means a halving of the scattering of the system error with respect to the non-corrected values from FIG. 13, and this distinctly increases the reliability of the measurement for the user.

Example 2: Obtaining a Piece of Correction Information for the Correction of an Analyte Measurement and Example of a Correction An example of a correction of a glucose measurement on the basis of a piece of correction information generated from a diffusion of label is described exemplarily below. In this connection, it is generally applicable that the reflectance R is a function F of the temperature T and Hct both in the case of measurement of the label and in the case of measurement of an analyte signal, and in both cases the same dependence emerges:

$$R[\%] = F(T, Hct) \qquad (3).$$

Since the influences of the individual interfering variables of temperature and of Hct generally form a joint interfering variable T×Hct, since in many cases the influences of temperature and of Hct are not to be separated but to be corrected together and since the influences of temperature and of Hct on the measured reflectance R are generally contrary (see, e.g., FIG. 11), the following can be applied:

$$R[\%] = F(T \times Hct) \quad (4).$$

The function F represents a calibration curve that can be ascertained from a measurement of label analogously to the measurements of a diffusion of label that were described above in connection with FIGS. 11-13. For example, a series of measurements can be recorded analogously to the measurements in FIG. 11, and the calibration curve can be determined therefrom. As can be seen from the graph in FIG. 11, the calibration curve F can be described in many cases as a line, having the equation:

$$F(R_{Label}) = a + m \cdot R_{Label} \quad (5).$$

In this connection, a represents an axis intercept or offset, whereas m describes a slope of the calibration curve. $R_{Label}$ represents a measured reflectance of the diffusable label at a particular concentration of the analyte, a particular temperature and a particular Hct. From the measurement points of the series of measurements in FIG. 11, it is possible to determine the parameters a and m by an appropriate fit.

With this known calibration curve, it is then possible to generate a piece of correction information in the case of an analyte measurement from an individual measurement or multiple measurements of a label reflectance $R_{Label}$ (i.e., a reflectance caused or influenced by the label and its diffusion in the sample). By means of this piece of correction information, it is then possible to correct a measured analyte reflectance $R_{Analyte}$ (i.e., a reflectance caused or influenced by the detection reaction) and to convert it into a corrected or actual analyte reflectance $R_{Analyte}^*$:

$$R_{Analyte}^* = R_{Analyte} - F(R_{Label}) \quad (6);$$

$$R_{Analyte}^* = R_{Analyte} - (a + m \cdot R_{Label}) \quad (7).$$

This corrected analyte reflectance can then, by means of a further calibration curve obtained from comparative measurements, be transformed or converted into an analyte concentration such as a glucose concentration.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

| Listing of reference numbers: | |
|---|---|
| 50 | Test element |
| 60 | Test support |
| 100 | Test field |
| 101 | Barrier |
| 102 | Test chemistry |
| 104 | Label |
| 104' | Label |
| 106 | Partition layer |
| 107 | Sample input side |
| 108 | Wetting |

| Listing of reference numbers: | |
|---|---|
| 110 | Sample/blood |
| 112 | Supernatant |
| 114 | $1^{st}$ region |
| 116 | $2^{nd}$ region |
| 117 | Analyte |
| 118 | Test chemistry layer/reactive layer |
| 120 | Label layer |
| 122 | Pigment layer |
| 130 | $1^{st}$ light source |
| 140 | $2^{nd}$ light source |
| 150a | Light of the $1^{st}$ light source |
| 150b | Light of the $2^{nd}$ light source |
| 160a | Reflected light from $1^{st}$ light source |
| 160b | Reflected light from $2^{nd}$ light source |
| 170 | $1^{st}$ detector |
| 175 | $1^{st}$ evaluation unit |
| 180 | $2^{nd}$ detector |
| 185 | $2^{nd}$ evaluation unit |
| 188 | Housing |
| 189 | Opening |
| 190 | Device |
| 200 | Intensity scale |
| 202 | Time scale |
| 204 | $1^{st}$ family of curves |
| 204a | 0 mg/dl gluc |
| 204b | 550 mg/dl gluc |
| 206 | $2^{nd}$ family of curves |
| 206a | 0 mg/dl gluc |
| 206b | 550 mg/dl gluc |
| 208 | $3^{rd}$ family of curves |
| 208a | 0 mg/dl gluc |
| 208b | 550 mg/dl gluc |
| 210 | $4^{th}$ family of curves |
| 210a | H$_2$O |
| 210b | Blood |
| 212 | $5^{th}$ family of curves |
| 212a | H$_2$O |
| 212b | Blood |
| 214 | $6^{th}$ family of curves |
| 214a | H$_2$O |
| 214b | Blood |
| 216 | 0.05% erioglaucine |
| 218 | 0.1% erioglaucine |
| 220 | 0.05% erioglaucine |
| 222 | 0.1% erioglaucine |
| 224 | 0.05% erioglaucine |
| 226 | 0.1% erioglaucine |
| 228 | Family of points having 25% Hct |
| 230 | Family of points having 45% Hct |
| 232 | Family of points having 65% Hct |
| 234 | Measurement point for temperature |
| 236 | Measurement point for Hct |
| 238 | Fitted line |

The invention claimed is:

1. A test element for determining at least one analyte concentration in a sample having at least one interfering variable, the test element comprising:

at least one test chemistry on a test support of the test element, wherein the at least one test chemistry is configured to carry out at least one detectable reaction with at least one analyte, wherein the test chemistry is completely or partly contained in at least one first region of the test support of the test element; and at least one diffusable label in the at least one first region of the test element, wherein the at least one diffusable label is configured to diffuse at least partly from the at least one first region of the test element into at least one second region of the test element, wherein the at least one test chemistry and the at least one diffusable label provide at least one piece of correction information from a detected diffusion of the at least one diffusable label, the at least one piece of correction information accounting for an influence of the at least one interfering variable and accounting for a general relationship between the at least one interfering variable and diffusion of the at least one diffusable label, wherein the at least one interfering variable is one or more of a temperature of the sample, a temperature of a testing environment, and hematocrit of the sample, and wherein the general relationship is obtained from at least one, predetermined calibration measurement.

2. The test element of claim 1, wherein the at least one test chemistry comprises at least one enzyme.

3. The test element of claim 2, wherein the at least one enzyme is selected from the group consisting of glucose dehydrogenase and glucose oxidase.

4. The test element of claim 1, wherein the at least one diffusable label is a dye.

5. The test element of claim 4, wherein the dye comprises at least one optically detectable dye.

6. The test element of claim 5, wherein the at least one optically detectable dye is hydrophilic or water-soluble.

7. The test element of claim 6, wherein the at least one optically detectable dye is selected from the group consisting of cyanine dyes, azo dyes, sulfone dyes, and a combination of at least two thereof.

8. The test element of claim 1, wherein the at least one diffusable label is selected from the group consisting of erioglaucine, indigo carmine, hydroxynaphthol blue, 1,1-diethyl-4,4-carbocyanine iodide, amaranth, and a combination of at least two thereof.

9. The test element of claim 8, wherein the at least one diffusable label is erioglaucine or hydroxynaphthol blue.

10. The test element of claim 1, wherein the at least one test chemistry comprises an enzyme selected from the group consisting of glucose dehydrogenase and glucose oxidase, and wherein the at least one diffusable label is selected from the group consisting of erioglaucine, indigo carmine, hydroxynaphthol blue, 1,1-diethyl-4,4-carbocyanine iodide, amaranth, and a combination of at least two thereof.

11. The test element of claim 1, further comprising at least one test field having at least one test chemistry layer that comprises the at least one test chemistry.

12. The test element of claim 1, wherein the at least one diffusable label is arranged completely or partly separately from the at least one test chemistry.

13. The test element of claim 1, wherein the at least one diffusable label does not react with one or both of the at least one analyte or the at least one test chemistry, and wherein a diffusion rate of the at least one diffusable label is substantially independent of the at least one analyte concentration.

14. The test element of claim 1, wherein the at least one diffusable label absorbs light within a wavelength range from about 300 nm to about 800 nm.

15. The test element of claim 1, wherein the at least one interfering variable is selected from the group consisting of a temperature of the sample, a temperature of the test element, a proportion of constituents of at least one substance in the sample, and a combination of at least two thereof.

16. The test element of claim 1, wherein the at least one diffusable label is a first diffusible label and the test element further comprises at least one second diffusable label different from the first diffusable label, wherein a diffusion rate of the first diffusable label is influenced by at least one first property of the sample, and wherein a diffusion rate of the at least one second diffusable label is influenced by at least one second property of the sample different from the at least one first property.

* * * * *